(12) United States Patent
Lin et al.

(10) Patent No.: US 11,673,125 B2
(45) Date of Patent: *Jun. 13, 2023

(54) METAL OXIDE-SUPPORTED EARTH-ABUNDANT METAL CATALYSTS FOR HIGHLY EFFICIENT ORGANIC TRANSFORMATIONS

(71) Applicant: The University of Chicago, Chicago, IL (US)

(72) Inventors: Wenbin Lin, Chicago, IL (US); Kuntal Manna, Chicago, IL (US); Pengfei Ji, Chicago, IL (US); Takahiro Sawano, Chicago, IL (US); Zekai Lin, Parsippany, NJ (US)

(73) Assignee: The University of Chicago, Chicago, IL (US)

( * ) Notice: Subject to any disclaimer, the term of this patent is extended or adjusted under 35 U.S.C. 154(b) by 598 days.

This patent is subject to a terminal disclaimer.

(21) Appl. No.: 16/314,326

(22) PCT Filed: Aug. 18, 2017

(86) PCT No.: PCT/US2017/047531
§ 371 (c)(1),
(2) Date: Dec. 28, 2018

(87) PCT Pub. No.: WO2018/035421
PCT Pub. Date: Feb. 22, 2018

(65) Prior Publication Data
US 2020/0324276 A1  Oct. 15, 2020

Related U.S. Application Data

(60) Provisional application No. 62/470,920, filed on Mar. 14, 2017, provisional application No. 62/376,671, filed on Aug. 18, 2016.

(51) Int. Cl.
*B01J 31/02* (2006.01)
*B01J 27/128* (2006.01)
(Continued)

(52) U.S. Cl.
CPC .......... *B01J 27/128* (2013.01); *B01J 31/121* (2013.01); *B01J 37/04* (2013.01); *B01J 2231/44* (2013.01);
(Continued)

(58) Field of Classification Search
None
See application file for complete search history.

(56) References Cited

U.S. PATENT DOCUMENTS 2,891,094 A  6/1959  Karkalits, Jr. et al.
3,027,398 A  3/1962  Foohey
(Continued)

FOREIGN PATENT DOCUMENTS

CN  1207105 A  2/1999
CN  1717279 A  1/2006
(Continued)

OTHER PUBLICATIONS

Bart et al., "Preparation and molecular and electronic structures of iron(0) dinitrogen and silane complexes and their application to catalytic hydrogenation and hydrosilation," J. Am. Chem. Soc., 126, 13794-13807 (2004).
(Continued)

*Primary Examiner* — Yun Qian
(74) *Attorney, Agent, or Firm* — Jenkins, Wilson, Taylor & Hunt, P.A.

(57) ABSTRACT

Surface hydroxyl groups on porous and nonporous metal oxides, such as silica gel and alumina, were metalated with catalyst precursors, such as complexes of earth abundant metals (e.g., Fe, Co, Cr, Ni, Cu, Mn and Mg). The metalated
(Continued)

metal oxide catalysts provide a versatile family of recyclable and reusable single-site solid catalysts for catalyzing a variety of organic transformations. The catalysts can also be integrated into a flow reactor or a supercritical fluid reactor.

3 Claims, 3 Drawing Sheets

(51) Int. Cl.
  *B01J 31/12* (2006.01)
  *B01J 37/04* (2006.01)
(52) U.S. Cl.
  CPC .... *B01J 2231/643* (2013.01); *B01J 2231/645* (2013.01); *B01J 2231/646* (2013.01); *B01J 2531/845* (2013.01); *B01J 2531/847* (2013.01)

(56) References Cited

U.S. PATENT DOCUMENTS

| | | | |
|---|---|---|---|
| 3,270,057 | A | 8/1966 | Cooke et al. |
| 3,308,086 | A | 3/1967 | Wartman |
| 3,499,034 | A | 3/1970 | Gonzalez |
| 3,636,108 | A | 1/1972 | Brake |
| 3,636,152 | A | 1/1972 | Szigeth |
| 4,185,036 | A | 1/1980 | Cossaboon |
| 4,252,689 | A | 2/1981 | Miya |
| 4,265,834 | A | 5/1981 | Birkenstock et al. |
| 4,273,945 | A | 6/1981 | Heilen et al. |
| 4,429,155 | A | 1/1984 | Goetz et al. |
| 4,960,941 | A | 10/1990 | Vedage et al. |
| 5,008,090 | A * | 4/1991 | Joy, III ............... B01J 37/04 423/212 |
| 5,189,223 | A | 2/1993 | Ogata et al. |
| 5,286,898 | A | 2/1994 | Gustafson et al. |
| 5,319,129 | A | 6/1994 | Gustafson et al. |
| 5,360,934 | A | 11/1994 | Vedage et al. |
| 6,043,395 | A | 3/2000 | Langer et al. |
| 6,331,601 | B1 | 12/2001 | Hlatky |
| 6,639,031 | B1 | 10/2003 | Poetsch et al. |
| 6,888,021 | B2 | 5/2005 | Brunner et al. |
| 10,118,169 | B2 | 11/2018 | Lin et al. |
| 2002/0160027 | A1 | 10/2002 | Buchholz et al. |
| 2007/0281854 | A1* | 12/2007 | Harbour ............. B01J 20/28083 502/156 |
| 2008/0139383 | A1 | 6/2008 | Ryu |
| 2011/0060169 | A1 | 3/2011 | Kaizik et al. |
| 2012/0296111 | A1 | 11/2012 | Konigsmann et al. |
| 2012/0315199 | A1 | 12/2012 | Neltner et al. |
| 2014/0155670 | A1* | 6/2014 | Slowing .............. B01J 23/745 585/733 |
| 2014/0275686 | A1 | 9/2014 | Hock et al. |
| 2015/0031908 | A1 | 1/2015 | Bury et al. |
| 2016/0168283 | A1 | 6/2016 | Coperet et al. |
| 2017/0173572 | A1 | 6/2017 | Lin et al. |
| 2017/0182486 | A1 | 6/2017 | Lin et al. |
| 2018/0361370 | A1 | 12/2018 | Lin et al. |

FOREIGN PATENT DOCUMENTS

| | | | |
|---|---|---|---|
| CN | 101376104 | A | 3/2009 |
| CN | 102712559 | A | 10/2012 |
| CN | 102791746 | A | 11/2012 |
| CN | 104445079 | A | 3/2015 |
| DE | 1106319 | | 5/1961 |
| DE | 1277232 | | 9/1968 |
| DE | 1949296 | | 4/1971 |
| DE | 1643856 | | 11/1971 |
| DE | 2538253 | | 10/1976 |
| DE | 2823165 | | 11/1979 |
| DE | 2832699 | | 2/1980 |
| EP | 011090 | B1 | 1/1982 |
| EP | 0053818 | | 6/1982 |
| EP | 0968996 | | 1/2000 |
| EP | 1479686 | A1 | 11/2004 |
| EP | 1819129 | A2 | 8/2007 |
| WO | WO 2012/025559 | A2 | 3/2012 |
| WO | WO2014/053618 | | 4/2014 |
| WO | WO 2015/069926 | A1 | 5/2015 |
| WO | WO 2015/149072 | A1 | 10/2015 |
| WO | WO 2017/066328 | A1 | 4/2017 |

OTHER PUBLICATIONS

Bellow et al., Reactivity Modes of an Iron Bis(alkoxide) Complex with Aryl Azides.
Chen et al., "Selective Catalytic Hydrogenation of Heteroarenes with N-Graphene-Modified Cobalt Nanoparticles (Co3O4—Co/NGr@α-Al2O3)," J. Am. Chem. Soc., 137, 11718-11724 (2015).
Chirik et al., Getting Down to Earth: The Renaissance of Catalysis with Abundant.
Crabtree, "Iridium Compounds in Catalysis," Acc. Chem. Res., 12, 331-337 (1979).
D'Souza et al., "Preparation of silica- and carbon-supported cobalt by electrostatic adsorption of Co(III) hexammines," Journal of Catalysis, 248, 165-174 (2007).
Hudson et al., "Highly efficient iron(0) nanoparticle-catalyzed hydrogenation in water in flow," Green Chem., 15, 2141-2148 (2013).
Jiao et al., "The synthesis of highly dispersed noble and base metals on silica via strong electrostatic adsorption: II. Mesoporous silica SBA-15," Journal of Catalysis, 260, 342-350 (Nov. 1, 2017).
Kelsen et al., "The use of ultrasmall iron(0) nanoparticles as catalysts for the selective hydrogenation of unsaturated C—C bonds," Chen. Commun., 49, 3416-3418 (2013).
Mokhov et al., Colloid and Nanodimensional Catalysts in Organic Synthesis.
Notification of Transmittal of the International Search Report and the Written Opinion of the International Searching Authority, or the Declaration for International Application No. PCT/US17/047531 dated Feb. 13, 2018.
Notification Concerning Transmittal of International Preliminary Report on Patentability for International Application No. PCT/US2017/047531, dated Feb. 28, 2019.
Schreier et al., "A fundamental study of Pt tetrammine impregnation of silica 1. The electrostatic nature of platinum adsorption," Journal of Catalysis, 225, 190-202 (2004).
Stein et al., "Iron Nanoparticles Supported on Chemically-Derived Graphene: Catalytic Hydrogenation with Magnetic Catalyst Separation," Adv. Synth. Catal., 353, 523-527 (2011).
Welther et al., "Iron(0) Particles: Catalytic Hydrogenations and Spectroscopic Studies," ChemCatChemm 4, 1088-1093 (2012).
Zhang et al., "Mild and homogeneous cobalt-catalyzed hydrogenation of C=C, C=O, and C=N bonds," Angew. Chem. Int. Ed., 51, 12102-12106 (2012).
Anonymous: "Sodium triethylborohydride—Wikipedia," Sep. 3, 2015, XP055648189, Retrieved from the Internet: URL: https://en.wikipedia.org/w/index.php?title=Sodium_triethylborohydride&oldid=679206155 [retrieved on Dec. 2, 2019].
European Search Report corresponding to European application No. 17842185 dated Dec. 9, 2019.
Communication of European publication number corresponding to European Patent Application No. 17842185.5 dated Apr. 3, 2019.
Arrowsmith et al., "Magnesium-Catalyzed Hydroboration of Pyridines," Organometallics, 30 , 5556-5559 (2011).
Behrsing et al., "Cerium acetylacetonates—new aspects, including the lamellar clathrate [Ce(acac)4] 10H2O," Inorg. Chem. Acta, 352, 229-237 (2003).
Beletskaya et al., "Hydroborations Catalysed by Transition Metal Complexes," Tetrahedron, vol. 53, pp. 4957-5026 (1997).
Bull et al., "Synthesis of Pyridine and Dihydropyridine Derivatives by Regio- and Stereoselective Addition to N-Activated Pyridines," Chem. Rev., 112, 2642-2713 (2012).
Burgess et al., "Transition-Metal-Promoted Hydroborations of Alkenes, Emerging Methodology for Organic Transformations," Chem. Rev., 91, 1179-1191 (1991).

(56) References Cited

OTHER PUBLICATIONS

Cao et al., "End Group Functionalization of PFpP Macromolecules via Fp Migration Insertion Reactions," Macromol. Rapid Commun., 37, 246-250 (2016).

Casey et al., "An Efficient and Chemoselective Iron Catalyst for the Hydrogenation of Ketones," J. Am. Chem. Soc., 129, 5816-5817 (2007).

Chakraborty et al., "Iron-Based Catalysts for the Hydrogenation of Esters to Alcohols," J. Am. Chem. Soc., 136, 7869-7872 (2014).

Chakraborty et al., "Nickel and Iron Pincer Complexes as Catalysts for the Reduction of Carbonyl Compounds," Acc. Chem. Res., vol. 48, pp. 1995-2003 (2015).

Choi et al., "Chemical Environment Control and Enhanced Catalytic Performance of Platinum Nanoparticles Embedded in Nanocrystalline Metal-Organic Frameworks," J. Am. Chem. Soc., 137, 7810-7816(2015).

Comito et al., "Single-Site Heterogeneous Catalysts for Olefin Polymerization Enabled by Cation Exchange in a Metal-Organic Framework," J. Am. Chem. Soc. 138, 10232-10237 (2016) (DOI: 10.1021/jacs.6b05200).

Das et al., "Functional Mixed Metal-Organic Frameworks with Metalloligands," Angew. Chem., Int. Ed., vol. 50, pp. 10510-10520 (2011).

de Quadras et al, "Monophosphine and diphosphine ligands for diplatinum polyynediyl complexes: Efficient syntheses of new functionality-containing systems and model compounds," J. of Organomet. Chem., 692, 1859-1870 (2007).

Delacroix et al., "Hydrophosphination of Unactivated Alkenes, Dienes and Alkynes: A Versatile and Valuable Approach for the Synthesis of Phosphines," Current Organic Chemistry, 9, 1851-1882 (2005).

Dolomanov et al., "OLEX2: a complete structure solution, refinement and analysis program," Journal of Applied Crystallography, 42, 339-341 (2009).

Dudnik et al., "Atom-efficient regioselective 1,2-dearomatization of functionalized pyridines by an earth-abundant organolanthanide catalyst," Nat. Chem., 6, 1100-1107 (2014).

Edraki et al., "Dihydropyridines: evaluation of their current and future pharmacological applications," Drug Discov. Today, 14, 1058-1066 (2009).

Evans et al., "Crystal Engineering of NLO Materials Based on Metal-Organic," Acc. Chem. Res., vol. 35, No. 7, pp. 511-522 (2002).

Falkowski et al., "Privileged Phosphine-Based Metal-Organic Frameworks for Broad-Scope Asymmetric Catalysis," J. Am. Chem. Soc., vol. 136, pp. 5213-5216 (2014).

Fan et al., "Organoborane Catalyzed Regioselective 1,4-Hydroboration of Pyridines," J. Am. Chem. Soc., 137, 4916-4919 (2015).

Fei et al., "Reusable Oxidation Catalysis Using Metal-Monocatecholato Species in a Robust Metal-Organic Framework," J. Am. Chem. Soc., 136, 4965-4973 (2014).

Fendrick et al., "Manipulation of Organoactinide Coordinative Unsaturation and Stereochemistry. Properties of Chelating Bis(polymethylcyclopentadienyl) Hydrocarbyls and Hydrides," J. Organometallics, 3, 819-821 (1984).

Furukawa et al., "The Chemistry and Applications of Metal-Organic Frameworks," Science, vol. 341, pp. 1230444-1-1230444-12 (2013).

Furukawa et al., "Water Adsorption in Porous Metal-Organic Frameworks and Related Materials," J. Am. Chem. Soc., vol. 136, pp. 4369-4381 (2014).

Gascon et al., "Metal Organic Framework Catalysis: Quo vadis?," ACS Catal., 4, 361-378 (2013).

Genna et al., "Heterogenization of Homogeneous Catalysts in Metal-Organic Frameworks via Cation Exchange," J. Am. Chem. Soc., vol. 135, 10586-10589 (2013).

Ghebreab et al., "Intermolecular Zirconium-Catalyzed Hydrophosphination of Alkenes and Dienes with Primary Phosphines," J. Am. Chem. Soc., 136, 9240-9243 (2014).

Gonzalez et al., "Single-Crystal-to-Single-Crystal Metalation of a Metal-Organic Framework: A Route toward Structurally Well-Defined Catalysts," Inorg. Chem., 54, 2995-3005 (2015).

Gromada et al., "Group 3 metal catalysts for ethylene and α-olefin polymerization," Coord. Chem. Rev., 248, 397-410 (2004).

Hayashi et al., "Fluoride-mediated phosphination of alkenes and alkynes by silylphosphines," Tetrahedron Lett., 45, 9167-9169 (2004).

Henschel et al., "Catalytic properties of MIL-101," Chem. Commun., 4192-4194 (2008).

Hong et al., "Organolanthanide-Catalyzed Hydroamination," J. Acc. Chem. Res., 37, 673-686 (2004).

Hou et al., "Recent developments in organolanthanide polymerization catalysts," Coord. Chem. Rev., 231, 1-22 (2002).

Hwang et al., "Amine Grafting on Coordinatively Unsaturated Metal Centers of MOFs: Consequences for Catalysis and Metal Encapsulation," Angew. Chem., Int. Ed., 47, 4144-4148 (2008).

Intemann et al., "Multinuclear Magnesium Hydride Clusters: Selective Reduction and Catalytic Hydroboration of Pyridines," Organometallics, 33, 5722-5729 (2014).

International Search Report and Written Opinion corresponding to International application No. PCT/US2016/056649 dated Dec. 30, 2016.

IPRP corresponding to International Application No. PCT/US2016/056649 dated Apr. 26, 2018.

Jagadeesh et al., "Nanoscale Fe2O3-Based Catalysts for Selective Hydrogenation of Nitroarenes to Anilines," Science, 342, 1073-1076 (2013).

Jeske et al., "Highly Reactive Organolanthanides. Synthesis, Chemistry, and Structures of 4f Hydrocarbyls and Hydrides with Chelating Bis(polymethylcyclopentadienyl) Ligands," J. Am. Chem. Soc., 107, 8103-8110 (1985).

Ji et al., "Organometallic Ce6(μ3-O)4(μ3-OLi)4(H)6(THF)6 Secondary Building Units in a Cerium Metal-Organic Framework for Catalytic Hydroboration and Hydrophosphination," author manuscript, pp. 1-5 (2016).

Ji et al., Supporting Information for "Organometallic Ce6(μ3-O)4(μ3-OLi)4(H)6(THF)6 Secondary Building Units in a Cerium Metal-Organic Framework for Catalytic Hydroboration and Hydrophosphination," author manuscript, pp. S1-S28 (2016).

Jiang et al., "Brønsted Acidity in Metal-Organic Frameworks," Chem. Rev., 115, 6966-6997 (2015).

Johnson et al., "Industrial-Scale Synthesis and Applications of Asymmetric Hydrogenation Catalysts," Acc. Chem. Res., 40, 1291-1299 (2007).

Kesanli et al., "Chiral porous coordination networks: rational design and applications in enantioselective processes," Coord. Chem. Rev., vol. 246, pp. 305-326 (2003).

Klet et al., "Single-Site Organozirconium Catalyst Embedded in a Metal-Organic Framework," J. Am. Chem. Soc., 137, 15680-15683 (2015).

Klet et al., "Synthetic Access to Atomically Dispersed Metals in Metal-Organic Frameworks via a Combined Atomic-Layer-Deposition-in-MOF and Metal-Exchange Approach," Chem. Mater., 28, 1213-1219 (2016).

Knowles et al., "Pioneering Perspectives on Asymmetric Hydrogenation," Acc. Chem. Res., vol. 40, pp. 1238-1239 (2007).

Kobayashi et al., "Rare-Earth Metal Triflates in Organic Synthesis," Chem. Rev., vol. 102, pp. 2227-2302 (2002).

Koshti et al., "Contemporary avenues in catalytic P H bond addition reaction: A case study of hydrophosphination," Coord. Chem. Rev., vol. 265, pp. 52-73 (2014).

Kreno et al., "Metal-Organic Framework Materials as Chemical Sensors," Chem. Rev., vol. 112, 1105-1125 (2012).

Kung et al., "Metal-Organic Framework Thin Films as Platforms for Atomic Layer Deposition of Cobalt Ions to Enable Electrocatalytic Water Oxidation," ACS Appl. Mater. Interfaces, vol. 7, pp. 28223-28230 (2015).

Lagaditis et al., "Iron(II) Complexes Containing Unsymmetrical P—N—P' Pincer Ligands for the Catalytic Asymmetric Hydrogenation of Ketones and Imines," J. Am. Chem. Soc., vol. 136, pp. 1367-1380 (2014).

(56) References Cited

OTHER PUBLICATIONS

Lammert et al., "Cerium-based metal organic frameworks with UiO-66 architechture: synthesis, properties and redox catalytic activity," Chem. Commun., vol. 51, pp. 12578-12581 (2015).
Lan et al., "A Luminescent Microporous Metal-Organic Framework for the Fast and Reversible Detection of High Explosives," Angew. Chem., Int. Ed., vol. 48, pp. 2334-2338 (2009).
Langer et al., "Efficient Hydrogenation of Ketones Catalyzed by an Iron Pincer Complex," Chem., Int. Ed., vol. 123, pp. 2120-2124 (2011).
Lavilla, "Recent developments in the chemistry of dihydropyridines," J. Chem. Soc., Perkin Trans. I, pp. 1141-1156 (2002).
Leyva-Pérez et al., "Copper(I)-catalyzed hydrophosphination of styrenes," J. Organomet. Chem., vol. 696, pp. 362-367 (2011).
Li et al., "A strategy toward constructing a bifunctionalized MOF catalyst: post-synthetic modification of MOFs on organic ligands and coordinatively unsaturated metal sites," Chem. Commun. vol. 48, pp. 6151-6153 (2012).
Li et al. "Iron-, Cobalt-, and Nickel-Catalyzed Asymmetric Transfer Hydrogenation and Asymmetric Hydrogenation of Ketones," Acc. Chem. Res., vol. 48, pp. 2587-2598 (2015).
Li et al., "Metal-Organic Frameworks for Separations," Chem. Rev., vol. 112, pp. 869-932 (2012).
Liu et al., "FeCl2-catalyzed hydroboration of aryl alkenes with bis(pinacolato)diboron," J. RSC Adv., vol. 5, pp. 73705-73713 (2015).
Liu et al., "Metal-free aerobic oxidative coupling of amines to imines," Chemical Communications, vol. 47, pp. 10148-10150 (2011).
Liu et al., "Synthesis and migration insertion polymerization (MIP) of CpFe(CO)2(CH2)6PPh2(FpC6P) for PFpC6P: macromolecule stability, degradability and redox activity," Polym. Chem., vol. 5, pp. 6702-6709 (2014).
Mallat et al., "Asymmetric Catalysis at Chiral Metal Surfaces," Chem. Rev., vol. 107, pp. 4863-4890 (2007).
Manna et al., "Bipyridine- and Phenanthroline-Based Metal-Organic Frameworks for Highly Efficient and Tandem Catalytic Organic Transformations via Directed C—H Activation," J. Am. Chem. Soc., vol. 137, pp. 2665-2673 (2015).
Manna et al., "Chemoselective single-site Earth-abundant metal catalysts at metal-organic framework nodes," Nat. Commun., vol. 7, No. 12610, pp. 1-11, DOI: 10.1038/ncomms12610 (2016).
Manna et al., "Postsynthetic Metalation of Bipyridyl-Containing Metal-Organic Frameworks for Highly Efficient Catalytic Organic Transformations," J. Am. Chem. Soc., vol. 136, pp. 6566-6569 (2014).
Manna et al., "Salicylaidimine-Based Metal-Organic Framework Enabling Highly Active Olefin Hydrogenation with Iron and Cobalt Catalysts," J. Am. Chem. Soc., vol. 136, No. 38, pp. 13182-13185(2014).
McGuirk et al., "Turning on Catalysis: Incorporation of a Hydrogen-Bond-Donating Squaramide Moiety into a Zr Metal-Organic Framework," J. Am. Chem. Soc., vol. 137, pp. 919-925 (2015).
Metzger et al., "Selective Dimerization of Ethylene to 1-Butene with a Porous Catalyst," ACS Cent. Sci., vol. 2, pp. 148-153 (2016).
Mikhailine et al., "Efficient Asymmetric Transfer Hydrogenation of Ketones Catalyzed by an Iron Complex Containing a P—N—N—P Tetradentate Ligand Formed by Template Synthesis," J. Am. Chem. Soc., 131, 1394-1395 (2009).
Molander et al., "Lanthanocene Catalysts in Selective Organic Synthesis," Chem. Rev., vol. 102, 2161-2185 (2002).
Morris, "Exploiting Metal-Ligand Bifunctional Reactions in the Design of Iron Asymmetric Hydrogenation Catalysts," Acc. Chem. Res., 48, 1494-1502 (2015).
Moulton et al., "From Molecules to Crystal engineering: Supramolecuiar Isomerism and Polymorphism in Network Solids," Chem. Rev., vol. 101, pp. 1629-1658 (2001).
Müller et al., "Hydroamination: Direct Addition of Amines to Alkenes and Alkynes," Chem. Rev., 108, 3795-3892 (2008).
Nair et al., "Cerium(IV) Ammonium Nitrate—A Versatile Single-Electron Oxidant," Chem. Rev., 107, 1862-1891 (2007).
Nair et al., "Recent Advances in Synthetic Transformations Mediated by Cerium(IV) Ammonium Nitrate," J. Acc. Chem. Res., 37, 21-30 (2004).
Nakazawa et al., "Fe—H Complexes in Catalysis. In Iron Catalysis: Fundamentals and Applications," Plietker, B., Ed. Springer Berlin Heidelberg: Berlin, Heidelberg; pp. 27-81 (2011).
Nguyen et al., "Vanadium-Node-Functionalized UiO-66: A Thermally Stable MOF-Supported Catalyst for the Gas-Phase Oxidative Dehydrogenation of Cyclohexene," ACS Catalysis, vol. 4, No. 8, pp. 2496-2500 (2014).
Notice of Allowance corresponding to U.S. Appl. No. 15/767,862 dated Nov. 19, 2019.
Office Action corresponding to U.S. Appl. No. 15/767,862 dated Mar. 8, 2019.
Office Action corresponding to U.S. Appl. No. 15/767,862 dated Aug. 2, 2019.
Oshima et al., "Regioselective Synthesis of 1,2-Dihydropyridines by Rhodium-Catalyzed Hydroboration of Pyridines," J. Am. Chem. Soc., 134, 3699-3702 (2012).
Ouellet et al., "Enantioselective Organocatalytic Transfer Hydrogenation Reactions using Hantzsch Esters," Acc. Chem. Res., vol. 40, No. 12, pp. 1327-1339 (2007).
Park et al., "A versatile metal-organic framework for carbon dioxide capture and cooperative catalysis," Chem. Commun., 48, 9995-9997 (2012).
Peters et al., "Atomically Precise Growth of Catalytically Active Cobalt Sulfide on Flat Surfaces and within a Metal-Organic Framework via Atomic Layer Deposition," ACS Nano, 9, 8484-8490 (2015).
Piro et al., "The electrochemical behavior of cerium(III/IV) complexes: Thermodynamics, kinetics and applications in synthesis," Coord. Chem. Rev., 260, 21-36 (2014).
Pu et al., "A Carbon Dioxide Insertion Reaction into the Co—H Bond of Nitrogentris(triphenylphosphine)cobalt Hydride," J. Am. Chem. Soc., 90, 3896 (1968).
Pullen et al., "Enhanced Photochemical Hydrogen Production by a Molecular Diiron Catalyst Incorporated into a Metal-Organic Framework," J. Am. Chem. Soc., vol. 135, pp. 16997-17003 (2013).
Ravel et al., "Athena, Artemis, Hephaestus: data analysis for X-ray absorption spectroscopy using IFEFFIT," Journal of Synchrotron Radiation, vol. 12, pp. 537-541 (2005).
Rehr et al., "Theoretical approaches to x-ray absorption fine structure," Reviews of Modern Physics, vol. 72, No. 3, pp. 621-654 (2000).
Rösler et al., "A Highly Active and Easily Accessible Cobalt Catalyst for Selective Hydrogenation of C=O Bonds," J. Am. Chem. Soc., 137, 7998-8001 (2015).
Rossi et al., "Selective Formation of Secondary Amides via the Copper-Catalyzed Cross-Coupling of Alkylboronic Acids with Primary Amides," Org. Lett., 15, 2314-2317 (2013).
Rueping et al., "Advances in catalytic metal-free reductions: from bio-inspired concepts to applications in the organocatalytic synthesis of pharmaceuticals and natural products," Green Chem., 13, 1084-1105 (2011).
Saudan, "Hydrogenation Processes in the Synthesis of Perfumery Ingredients," Acc. Chem. Res., 40, 1309-1319 (2007).
Sawano et al., "Robust, Chiral, and Porous BINAP-Based Metal-Organic Frameworks for Highly Enantioselective Cyclization Reactions," J. Am. Chem. Soc., vol. 137, pp. 12241-12248 (2015b).
Sawano et al., "The first chiral diene-based metal-organic frameworks for highly enantioselective carbon-carbon bond formation reactions," Chem. Sci., vol. 6, pp. 7163-7168 (2015a).
Sheldrick, "A short history of SHELX," Acta Crystallographica Section A, vol. 64, pp. 112-122 (2008).
Sheldrick, "Crystal structure refinement with SHELXL," Acta Crystallographica Section C, vol. 71, pp. 3-8 (2015).
Shibasaki et al., "Lanthanide Complexes in Multifunctional Asymmetric Catalysis," N. Chem. Rev., 102, 2187-2209 (2002).

(56) References Cited

OTHER PUBLICATIONS

Shustova et al., "Selective Turn-On Ammonia Sensing Enabled by High-Temperature Fluorescence in Metal-Organic Frameworks with Open Metal Sites," J. Am. Chem. Soc., vol. 135, pp. 13326-13329 (2013).

Sridharan et al., "Cerium(IV) Ammonium Nitrate as a Catalyst in Organic Synthesis," Chem. Rev., 110, 3805-3849 (2010).

Stalzer et al., "Single-Face/All-cis Arene Hydrogenation by a Supported Single-Site d0 Organozirconium Catalyst," Angew. Chem., Int. Ed., 55, 5263-5267 (2016).

Stout et al., "Recent Advances in the Chemistry of Dihydropyridines," Chem. Rev., 82, 223-243 (1982).

Tanabe et al., "Postsynthetic modification of metal-organic frameworks—a progress report," Chem. Soc. Rev., 40, 498-519 (2011).

Thacker et al., "Robust and Porous β-Diketiminate-Functionalized Metal-Organic Frameworks for Earth-Abundant-Metal-Catalyzed C—H Amination and Hydrogenation," J. Am. Chem. Soc., 138, 3501-3509 (2016).

Thimmaiah et al., "Multi-component synthesis of 2-amino-6-(alkylthio)pyridine-3,5-dicarbonitriles using Zn(II) and Cd(II) metal-organic frameworks (MOFs) under solvent-free conditions," Author Manuscript, pp. 1-9, 2012 [published in final edited form in Tetrahedron Lett. 2012, vol. 53, No. 36, pp. 4870-4872].

Uemura et al., "Polymerization Reactions in Porous Coordination Polymers," Chem. Soc. Rev., vol. 38, No. 5, pp. 1228-1236 (2009).

Vermoortele et al., "An amino-modified Zr-terephthalate metal-organic framework as an acid-base catalyst for cross-aldol condensation," Chem. Commun., 47, 1521-1523 (2011).

Wang et al., "Asymmetric Hydrogenation of Heteroarenes and Arenes," Chemical Reviews, vol. 112, pp. 2557-2590 (2012).

Wang et al., "Metal-organic Frameworks as a Tunable Platform for Designing Functional Molecular Materials," author manuscript, pp. 1-32, 2013 [Published in final edited form in: J. Am. Chem. Soc. 2013, vol. 135, No. 36, pp. 13222-13234].

Wang et al., "Postsynthetic modification of metal-organic frameworks," Chem. Soc. Rev., 38, 1315-1329 (2009).

Wang et al., "Pt Nanoparticles@Photoactive Metal-Organic Frameworks: Efficient Hydrogen Evolution via Synergistic Photoexcitation and Electron Injection," J. Am. Chem. Soc., 134, 7211-7214 (2012).

Wiers et al., "A Solid Lithium Electrolyte via Addition of Lithium Isopropoxide to a Metal-Organic Framework with Open Metal Sites," J. Am. Chem. Soc., vol. 133, pp. 14522-14525 (2011).

Xin et al., "Access to 1,2-Dihydroisoquinolines through Gold-Catalyzed Formal [4+2] Cycloaddition," Chemistry—A European Journal, 20, 7926-7930 (2014).

Xu et al., "Acceptorless, Reversible Dehydrogenation and Hydrogenation of N-Heterocycles with a Cobalt Pincer Catalyst," ACS Catal., 5, 6350-6354 (2015).

Yang et al., "Metal-Organic Framework Nodes as Nearly Ideal Supports for Molecular Catalysts: NU-1000-and UiO-66-Supported Iridium Complexes," Journal of the American Chemical Society, vol. 137, No. 23, pp. 7391-7396 (2015).

Yoon et al., "Homochiral Metal-Organic Frameworks for Asymmetric Heterogeneous Catalysis," Chem. Rev., 112, 1196-1231 (2011).

Yu et al., "Catalytic Hydrogenation Activity and Electronic Structure Determination of Bis(arylimidazol-2-ylidene)pyridine Cobalt Alkyl and Hydride Complexes," Author manuscript, pp. 1-43, 2013 [Published in final edited form in: Journal of the American Chemical Society 2013, vol. 135, No. 35, pp. 13168-13184].

Zhang et al., "Asymmetric Hydrogenation of Ketones Catalyzed by Zeolite-supported Gelatin-Fe Complex," Polymer. Adv. Tech., 12, 642-646 (2001).

Zhang et al., "Developing Chiral Ligands for Asymmetric Hydrogenation," Acc. Chem. Res., 40, 1278-1290 (2007).

Zhang et al., "Highly Porous Zirconium Metal-Organic Frameworks with β-UH3-like Topology Based on Elongated Tetrahedral Linkers," J. Am. Chem. Soc., 138, 8380-8383 (2016).

Zhang et al., "Metal-Organic Frameworks Stabilize Solution-Inaccessible Cobalt Catalysts for Highly Efficient Broad-Scope Organic Transformations," J. Am. Chem. Soc., 138, 3241-3249 (2016).

Zhao et al., "Porous Metal-Organic Frameworks for Heterogeneous Biomimetic Catalysis," Acc. Chem. Res., 47, 1199-1207 (2014).

Zhao et al., "Solvothermal Synthesis of Multifunctional Coordination Polymers," Naturforsch., 65b, 976-998 (2010).

Zheng et al., "Transfer hydrogenation with Hantzsch esters and related organic hydride donors," Chem. Soc. Rev., 41, 2498-2518 (2012).

Zhou et al., "Borylation of primary and secondary alkyl bromides catalyzed by Cu2O nanoparticles," RSC Adv., 5, 46672-46676 (2015).

Ji et al., (2016), "Cerium-Hydride Secondary Building Units in a Porous Metal—Organic Framework for Catalytic Hydroboration and Hydrophosphination," Journ. Amer. Chem. Soc. 138, pp. 14860-14863.

Ji et al., (2016) "Single-Site Cobalt Catalysts at New Zr8(μ2-O)8(μ2-OH)4 Metal-OrganicFramework Nodes for Highly Active Hydrogenation of Alkenes,Imines, Carbonyls, and Heterocycles," Journ. Amer. Chem. Soc. 138, pp. 12234-12242.

Manna et al., "Metal-Organic Framework Nodes Support Single-Site Magnesium Alkyl Catalysts for Hydroboration and Hydroamination Reactions," Journal of the American Chemical Society, vol. 138, pp. 7488-7491 (2016).

Notification of the First Office Action and Search Report Corresponding to Chinese Application No. 201780049676.1 dated Jul. 5, 2021.

\* cited by examiner

METAL OXIDE-SUPPORTED EARTH-ABUNDANT METAL CATALYSTS FOR HIGHLY EFFICIENT ORGANIC TRANSFORMATIONS

RELATED APPLICATIONS

This application is a national phase application of PCT International Patent Application PCT/US2017/047531, filed Aug. 18, 2017; which claims the benefit of U.S. Provisional Patent Application Ser. No. 62/376,671, filed Aug. 18, 2016; and of U.S. Provisional Patent Application Ser. No. 62/470,920, filed Mar. 14, 2017; the disclosures of each of which are incorporated herein by reference in their entireties.

STATEMENT OF GOVERNMENT SUPPORT

This invention was made with government support under Grant No. CHE-1464941 from the National Science Foundation. The government has certain rights to this invention.

TECHNICAL FIELD

The presently disclosed subject matter relates to the metalation of metal oxides, such as porous or nonporous silica, silica gel, and porous or nonporous zirconia or titania, with catalyst precursors, such as Fe, Co, Cr, Mn, Ni, and Cu complexes, to provide highly active, single-site, earth abundant metal-based solid catalysts, the metalated metal oxide catalysts themselves, and their use as catalysts for a wide range of organic transformations, such as for the hydrogenation of olefins, ketones, imines, arenes, nitroarenes, and heterocycles, as well as for hydrosilation, C—C coupling reactions, ethylene oligomerization, hydromethylation, alkane metathesis, C—H bond activation and others.

ABBREVIATIONS

Å=angstrom
° C.=degrees Celsius
%=percentage
μL=microliter
μmol=micromole
Co=cobalt
Cr=chromium
Cu=copper
d=day
DMA=dimethylacetamide
DME=dimethoxyethane
DMF=dimethylformamide
DMSO=dimethylsulfoxide
EXFAS=extended x-ray absorption fine structure
Fe=iron
g=gram
GC=gas chromatography
h=hour
ICP-MS=inductively coupled plasma-mass spectrometry
M=molar
mg=milligram
Mg=magnesium
Me=methyl
min=minute
mL=milliliter
mM=millimolar
mmol=millimole
Mn=manganese
mol=moles
Ni=nickel
nm=nanometer
NMR=nuclear magnetic resonance
pin=pinacolate
Ph=phenyl
ppb=parts per billion
PXRD=powder x-ray diffraction
r.t. (or rt)=room temperature
TGA=thermogravimetric analysis
TOF=turnover frequency
TON=turnover number
XAFS=x-ray absorption fine structure
XAS=x-ray absorption spectroscopy
XANES=x-ray absorption near edge spectroscopy
Zr=zirconium

BACKGROUND

For decades, many organic transformations, such as hydrogenation reactions, have relied on precious metal catalysts. However, the low abundance, high price, and inherent toxicity of precious metals have led to intense interest in developing earth-abundant metal catalysts. See Chirik et al., Acc. Chem. Res., 2015, 48, 2495. Significant progress has been made in recent years on the development of base metal catalysts. For example, single-site hydrogenation catalysts based on iron, cobalt, nickel, or copper coordinated with sterically encumbered strong field nitrogen- or phosphorus-donor ligands have been reported. See for example, Bart et al., J. Am. Chem. Soc., 2004, 126, 13794-13807. However, each of these homogeneous base metal catalysts typically only hydrogenates a narrow class of substrates with limited turnover numbers. Furthermore, few examples of earth-abundant metal catalyzed hydrogenation reactions of imines and heterocycles exist and they generally involve harsh reaction conditions. See Chen et al., J. Am. Chem. Soc., 2015, 137, 11718-11724; and Zhanq et al., Angew. Chem. Int. Ed., 2012, 51, 12102-12106.

Homogeneous base metal catalysts typically rely on coordination of sterically bulky chelating ligands to prevent the formation of catalytically incompetent oligomeric species by shutting down the intermolecular decomposition pathways. Such steric protection is important for stabilizing weak-field ligand-coordinated metal catalysts, particularly for late first-row transition metals in a very weak field coordination environment consisting of oxygen-donor atoms. See Bellow et al., Organometallics, 2015, 34, 2917-2923. However, steric protecting groups often weaken metal-ligand binding and impede catalytic activity by preventing challenging hydrogenation substrates, such as tri- and tetra-substituted olefins, from accessing the catalytic sites. See Crabtree, Acc. Chem. Res., 1979, 12, 331-337. Immobilization of catalytic species in structurally regular porous solid supports can provide catalytic site isolation without relying on bulky ligands, thus offering an alternative route to obtaining highly active base metal catalysts. Significant efforts have been devoted to the development of zeolite-, silica- or graphene-supported iron- and cobalt-based heterogeneous hydrogenation catalysts (see, e.g., Chen et al., J. Am. Chem. Soc., 2015, 137, 11718-11724) and bare or protected metallic nanoparticle-based catalysts. See Stein et al., Adv. Synth. Catal., 2011, 353, 523-527; Welther et al., Chem Cat Chem, 2012, 4, 1088-1093; Hudson et al., Green Chem., 2013, 15, 2141-2148; Kelsen et al., Chem. Commun., 2013, 49, 3416-3418; and Mokhov et al., Russ. J. Gen. Chem., 2014, 84, 622-628. However, the activities and lifetimes of these heterogeneous hydrogenation catalysts can still be unsatisfactory.

Accordingly, there remains an ongoing need in the art for additional heterogeneous catalysts for catalysis. In particular, there is an ongoing need for additional catalysts comprising earth abundant/base metals that have good efficiency, good stability, and/or good recoverability. There is also an ongoing need for additional catalysts comprising earth abundant/base metals that can catalyze reactions at low catalyst loadings and/or at lower temperatures and pressures. Additionally, there is an ongoing need for additional heterogenous catalysts that are compatible with a wider range of substrates and/or that can catalyze a wider variety of reaction types.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

Disclosed herein in some embodiments is a method for preparing a catalyst, comprising: (a) providing a metal oxide comprising surface OH groups; and (b) reacting the metal oxide with a catalyst precursor, wherein the catalyst precursor is a compound of the formula $ML_nX$, wherein n is an integer from 0 to 5; X is H, alkyl, aralkyl, aryl, or halo; M is a catalytically active metal, and each L is independently selected from the group comprising H, halo, alkyl, aralkyl, aryl, heteroaryl, alkoxyl, and amine, thereby forming a catalyst comprising a $—O-M-L_x$ group, wherein x is an integer from 0 to 5.

In some embodiments, the method further comprises reacting the metal oxide with a base prior to the reacting the metal oxide with the catalyst precursor, thereby deprotonating all or a portion of the surface OH groups of the metal oxide to facilitate the metalation with the catalyst precursor. In some embodiments, the base is a salt of a Group 1 element and a carbanion, alkoxide, amide, or hydride, further optionally wherein the base is n-butyl lithium (n-BuLi), trimethylsilylmethyllithium ($LiCH_2SiMe_3$), or potassium tert-butoxide ($KO^tBu$).

In some embodiments, the metal oxide is selected from the group comprising porous or non-porous metal oxide, optionally wherein the metal oxide is silica gel, aerosol silica, mesoporous silica, zirconia, ceria, titania, alumina, or magnesia.

In some embodiments, M is selected from the group comprising iron, cobalt, chromium, nickel, copper, manganese, and magnesium. In some embodiments, the catalyst precursor is selected from the group consisting of $CoCl_2$, $FeBr_2$, $NiBr_2$, and $Me_2Mg$.

In some embodiments, the presently disclosed subject matter provides a catalyst prepared by a method comprising: (a) providing a metal oxide comprising surface OH groups; and (b) reacting the metal oxide with a catalyst precursor, wherein the catalyst precursor is a compound of the formula $ML_nX$, wherein n is an integer from 0 to 5; X is H, alkyl, aralkyl, aryl, or halo; M is a catalytically active metal, and each L is independently selected from the group comprising H, halo, alkyl, aralkyl, aryl, heteroaryl, alkoxyl, and amine, thereby forming a catalyst comprising a $—O-M-L_x$ group, wherein x is an integer from 0 to 5.

In some embodiments, the presently disclosed subject matter provides a composition comprising a metal oxide, wherein one or more metal or metalloid atom M' of the metal oxide is bonded to a group of the formula $—O-M-L_x$, wherein x is an integer from 0 to 5, M is a catalytically active metal, and each L is independently selected from the group comprising H, halo, alkyl, aralkyl, aryl, heteroaryl, alkoxy, and amine. In some embodiments, the 0 of the $—O-M-L_x$ group is an oxygen atom derived from a deprotonated terminal OH group or a deprotonated µ-OH group of the metal oxide.

In some embodiments, the metal or metalloid atom M' bonded to the $—O-M-L_x$ group is a metal or metalloid atom on the outer surface of a metal oxide particle or on the surface of a pore of a metal oxide particle. In some embodiments, the catalytically active metal M is free of decomposition due to disproportionation. In some embodiments, M is selected from the group comprising iron, cobalt, chromium, nickel, copper, manganese and magnesium.

In some embodiments, the metal oxide is a porous or non-porous silica, zironcia, ceria, titania, alumina, or magnesia and M' is selected from the group comprising Si, Zr, Ce, Al, and Mg. In some embodiments, the metal oxide is selected from silica gel, aerosol silica and mesoporous silica.

In some embodiments, each L is independently selected from the group comprising H, lower alkyl, and halo, optionally wherein lower alkyl is methyl. In some embodiments, one or more metal or metalloid atoms M' of the metal oxide are bonded to a group of the formula $—O-M-H$.

In some embodiments, the presently disclosed subject matter provides a method for preparing a compound comprising contacting a substrate capable of forming a product by catalytic transformation with a catalyst of a composition comprising a metal functionalized metal oxide as described herein, and/or a catalyst prepared by a method comprising: (a) providing a metal oxide comprising surface OH groups; and (b) reacting the metal oxide with a catalyst precursor, wherein the catalyst precursor is a compound of the formula $ML_nX$, wherein n is an integer from 0 to 5; X is H, alkyl, aralkyl, aryl, or halo; M is a catalytically active metal, and each L is independently selected from the group comprising H, halo, alkyl, aralkyl, aryl, heteroaryl, alkoxyl, and amine, thereby forming a catalyst comprising a $—O-M-L_x$ group, wherein x is an integer from 0 to 5.

In some embodiments, the method for preparing a compound comprises activating a metal functionalized metal oxide (e.g., a base-metal functionalized metal oxide) with an organoboron compound, optionally wherein the organoboron compound is sodium triethylborohydride, to form a metal hydride.

In some embodiments, the catalytic transformation is selected from the group comprising alkene hydrogenation, imine hydrogenation, nitrile hydrogenation, carbonyl hydrogenation, nitroarene hydrogenation, heterocycle hydrogenation, arene borylation, ethylene oligomerization, alkyne coupling, hydromethylation, alkane dehydrosilation, alkane metathesis, dehydrogenative alkyl C—H phosphination, pyridine functionalization, dehydrocoupling, hydrosilation of an olefin, ketone or aldehyde, oxidation of a primary alcohol, hydroamination, hydroformylation, C—H borylation, hydrogenation, hydroboration of a ketone or aldehyde, and C—H amination. In some embodiments, the reaction is conducted in a batch reactor, a flow reactor, or in a supercritical fluid reactor Accordingly, it is an object of the presently disclosed subject matter to provide metal oxides comprising a metalated surface OH group, wherein the metal of the metalated group is a catalytically active metal, such as Fe, Co, Cr, Ni, Cu, Mn, or Mg, methods of preparing the metalated metal oxides, and methods of using the metalated metal oxides as catalysts. This and other objects are achieved in whole or in part by the presently disclosed subject matter.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). A further understanding of the presently disclosed subject matter can be obtained by reference to an embodiment set forth in the illustrations of the accompanying drawings. Although the illustrated embodiment is merely exemplary of the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, but merely to clarify and exemplify the presently disclosed subject matter.

For a more complete understanding of the presently disclosed subject matter, reference is now made to the following drawings in which.

DETAILED DESCRIPTION

Figure 1A:
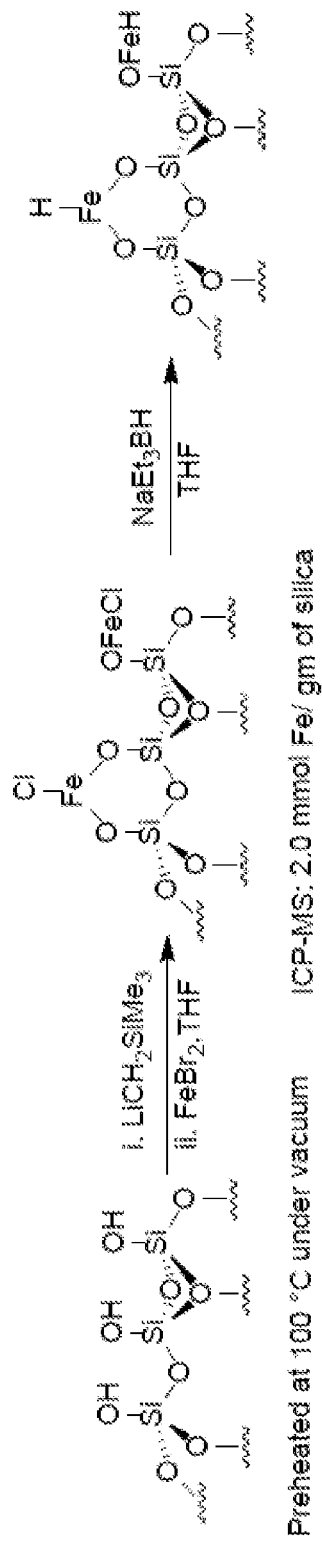
FIG. 1A is schematic drawing showing the metalation of surface silanol groups on mesoporous silica with iron. Silanol groups are first deprotanated using trimethylsilylmethyllithium ($LiCH_2SiMe_3$) and then reacted with iron bromide ($FeBr_2$). Reductive activation of the resulting iron halide provides a surface iron hydride.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. Although any methods, devices, and materials similar or equivalent to those described herein can be used in the practice or testing of the presently disclosed subject matter, representative methods, devices, and materials are now described. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a metal ion" includes a plurality of such metal ions, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

Numerical ranges recited herein by endpoints include all numbers and fractions subsumed within that range (e.g. 1 to 5 includes, but is not limited to, 1, 1.5, 2, 2.75, 3, 3.90, 4, and 5).

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and alkenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "heterocycle" refers to cyclic molecules or groups that contain one or more non-carbon atoms (e.g., O, N, S, Se, etc.) in the backbone of the ring structure. Heterocycle can include both heterocycloalkyl and heteroaryl.

"Heteroaryl" as used herein refers to an aryl group that contains one or more non-carbon atoms (e.g., O, N, S, Se, etc.) in the backbone of a ring structure. Nitrogen-containing heteroaryl moieties include, but are not limited to, pyridine, imidazole, benzimidazole, pyrazole, pyrazine, triazine, pyrimidine, and the like.

"Aralkyl" refers to an -alkyl-aryl group, optionally wherein the alkyl and/or aryl moiety is substituted. Exemplary aralkyl groups include, but are not limited to, benzyl (—$CH_2C_6H_5$) and phenylethyl (—$CH_2CH_2C_6H_5$).

The term "olefin" refers to a compound comprising a carbon-carbon double bond. The terms "olefin" and "alkene" can be used interchangeably.

The term "alkyne" as used herein refers to a compound comprising a carbon-carbon triple bond.

The term "imine" refers to a compound comprising a carbon-nitrogen double bond.

The term "arene" refers to an aromatic compound. Thus, the term "nitroarene" refers to an aromatic compound comprising a nitro substituent (e.g., nitrobenzene, nitronaphthalene, etc.).

The term "amino" refers to the group —$N(R)_2$ wherein each R is independently H, alkyl, substituted alkyl, aryl, substituted aryl, aralkyl, or substituted aralkyl. The terms "aminoalkyl" and "alkylamino" can refer to the group —$N(R)_2$ wherein each R is H, alkyl or substituted alkyl, and wherein at least one R is alkyl or substituted alkyl. "Arylamine" and "aminoaryl" refer to the group —$N(R)_2$ wherein each R is H, aryl, or substituted aryl, and wherein at least one R is aryl or substituted aryl, e.g., aniline (i.e., —$NHC_6H_5$).

The term "amine" refers to compounds or ligands for metals having the formula $N(R)_3$ wherein each R is independently H, alkyl, substituted alkyl, aryl, substituted aryl, aralkyl, or substituted aralkyl.

The terms "halo", "halide", or "halogen" as used herein refer to fluoro, chloro, bromo, and iodo groups.

The terms "hydroxy" and "hydroxyl" refer to the —OH group.

The terms "alkoxy" or "alkoxyl" refer to the —OR group, wherein R is a substituted or unsubstituted alkyl group. The terms "aryloxy" and "aryloxyl" refer to the group —OR, wherein R is an aryl or substituted aryl group.

The terms "mercapto" or "thiol" refer to the —SH group.

The term "carbonyl" refers to the group —C(=O)—. Exemplary types of compounds that comprise carbonyl groups include, but are not limited to, ketones, aldehydes, esters, carboxylic acids, esters, and amides.

The terms "carboxylate" and "carboxylic acid" can refer to the groups —C(=O)O$^-$ and —C(=O)OH, respectively. In some embodiments, "carboxylate" can refer to either the —C(=O)O$^-$ or —C(=O)OH group.

The term "ester" refers to a compound that comprises the group R'—O—C(=O)—R, wherein R and R' are independently alkyl, cycloalkyl, aralkyl, or aryl, wherein the alkyl, cycloalkyl, aralkyl, or aryl are optionally substituted.

The term "phosphonate" refers to the —P(=O)(OR)$_2$ group, wherein each R can be independently H, alkyl, substituted alkyl, aralkyl, substituted aralkyl, aryl, substituted aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

The term "silyl" refers to groups comprising silicon atoms (Si).

The term "isomer" as used herein refers to one of two or more molecules having the same number and kind of atoms and hence the same molecular weight, but differing in chemical structure. Isomers can differ in the connectivities of the atoms (structural isomers), or they can have the same atomic connectivities but differ only in the arrangement or configuration of the atoms in space (stereoisomers). "Stereoisomer" or "stereoisomers" refer to compounds that differ in chirality, e.g., that differ in the chirality of one or more stereocenters. Stereoisomers can include, but are not limited to, E/Z double bond isomers, enantiomers, and diastereomers. Structural moieties that, when appropriately substituted, can impart stereoisomerism include, but are not limited to, olefinic, imine or oxime double bonds; tetrahedral carbon, sulfur, nitrogen or phosphorus atoms; and allenic groups. Enantiomers are non-superimposable mirror images. A mixture of equal parts of the optical forms of a compound is known as a racemic mixture or racemate. Diastereomers are stereoisomers that are not mirror images.

The term "earth abundant metal" as used herein generally refers to catalytically active, generally nonprecious metals, such as to first row transition metals, i.e., Sc, Ti, V, Cr, Mn, Fe, Co, Ni, Cu, and Zn, as well as to Mg. In some embodiments, the term can further refer to base metals, such as Fe, Co, Ni, Cu, Zn and Pb. In particular, in some embodiments, the term "earth abundant metal" can refer to one or more of Fe, Co, Cr, Ni, Cu, Mn and Mg.

A "coordination complex" is a compound in which there is a coordinate bond between a metal ion and an electron pair donor, ligand or chelating group. Thus, ligands or chelating groups are generally electron pair donors, molecules or molecular ions having unshared electron pairs available for donation to a metal ion.

The term "coordinate bond" refers to an interaction between an electron pair donor and a coordination site on a metal ion resulting in an attractive force between the electron pair donor and the metal ion. The use of this term is not intended to be limiting, in so much as certain coordinate bonds also can be classified as have more or less covalent character (if not entirely covalent character) depending on the characteristics of the metal ion and the electron pair donor.

As used herein, the term "ligand" refers generally to a species, such as a molecule or ion, which interacts, e.g., binds, in some way with another species. More particularly, as used herein, a "ligand" can refer to a molecule or ion that binds a metal ion in solution to form a "coordination complex." See Martell, A. E., and Hancock, R. D., *Metal Complexes in Aqueous Solutions*, Plenum: New York (1996), which is incorporated herein by reference in its entirety. The terms "ligand" and "chelating group" can be used interchangeably.

Suitable ligands for metal ion complexes include compounds and groups with unshared electron pairs, such as, but not limited to, halo (i.e., —F, —Cl, —Br, and —I), —CO$_2$H, —NO$_2$, amine, hydroxyl, alkoxyl, aryloxyl, aralkyoxyl, thio, thioalkyl, —B(OH)$_2$, —SO$_3$H, PO$_3$H, phosphonate, and heteroatoms (e.g., nitrogen, oxygen, or sulfur) in heterocycles. In some embodiments, the metal ion ligand can be an alkyl, aryl, or aralkyl group.

As used herein, turnover number (TON) refers to the number of moles of substrate that a mole of catalyst can convert before being inactivated. As used herein, turnover frequency (TOF) refers to the number of moles of substrate that a mole of catalyst can convert in a particular unit of time (e.g., an hour).

As used herein, the term "stable" refers to a characteristic of a catalyst of the presently disclosed subject matter. A "stable" catalyst refers to a catalyst where the catalytic metal ion remains associated/bonded with a metal oxide carrier matrix during the catalytic reaction.

The term "organic solvent" as used herein refers to solvents used to dissolve reactants for organic transformations. Organic solvents include both protic and aprotic solvents. The term "aprotic solvent" refers to a solvent molecule which can neither accept nor donate a proton. Examples of aprotic organic solvents include, but are not limited to, ethyl acetate; carbon disulphide; ethers, such as, diethyl ether, tetrahydrofuran (THF), dimethoxylethane (DME), ethylene glycol dimethyl ether, dibutyl ether, diphenyl ether, MTBE, and the like; aliphatic hydrocarbons, such as hexane, pentane, cyclohexane, and the like; aromatic hydrocarbons, such as benzene, toluene, naphthalene, anisole, xylene, mesitylene, and the like; and symmetrical halogenated hydrocarbons, such as carbon tetrachloride, tetrachloroethane, and dichloromethane. Additional aprotic solvents include, for example, acetone, acetonitrile, butanone, butyronitrile, chlorobenzene, chloroform, 1,2-dichloroethane, dimethylacetamide (DMA), N,N-dimethylformamide (DMF), dimethylsulfoxide (DMSO), and 1,4-dioxane.

The term "protic solvent" refers to a solvent molecule which contains a hydrogen atom bonded to an electronegative atom, such as an oxygen atom or a nitrogen atom. Typical protic organic solvents include, but are not limited to, carboxylic acids, such as acetic acid, alcohols, such as methanol and ethanol, amines, am ides, and water.

II. General Considerations

The presently disclosed subject matter is based, in some aspects on the development of methods for metalating the surfaces of metal oxides with earth abundant metal catalyst precursors, such as, but not limited to, Fe, Co, Cr, Mn, Ni, and Cu complexes, to afford highly active single-site solid catalysts for organic transformations. See FIGS. 1A-1C. The presently disclosed earth-abundant metal functionalized solid materials can be prepared using readily available materials and can possess highly electron-deficient and coordinatively unsaturated metal centers that can catalyze organic reactions via σ-bond metathesis or other pathways. Thus, the presently disclosed materials provide a versatile family of single-site solid catalysts for a broad scope of organic transformations, including, but not limited to, the hydrogenation of olefins, alkynes, aldehydes, ketones, carboxylic acids and esters, imines, amides, nitriles, nitroarenes, and heterocycles, as well as hydrosilylation, C—C coupling reactions, ethylene oligomerization, hydromethylation, alkane metathesis, C—H bond activation, and others. The presently disclosed solid catalysts can also be integrated into a flow reactor or a supercritical fluid reactor to enable green manufacturing of chemicals.

Hydrogenation of unsaturated organic compounds is one of the most widely practiced metal-catalyzed reactions in organic synthesis and the chemical industry, with applications in the production of commodity chemicals, pharmaceuticals, and agrochemicals. For decades, hydrogenation reactions have relied on precious metal catalysts supported either on solid surfaces or by strong field ligands. However, the low abundance, high price, and inherent toxicity of precious metals have led to intense interest in developing earth-abundant metal catalysts. Significant progress has been made in recent years on the development of single-site hydrogenation catalysts based on iron, cobalt, nickel, or copper coordinated with sterically encumbered strong field nitrogen- or phosphorus-donor ligands. However, each homogeneous base metal catalyst typically only hydrogenates a narrow class of substrates with limited turnover numbers. Furthermore, few examples of earth-abundant metal catalyzed hydrogenation of imines and heterocycles exist, and those that do exist require harsh reaction conditions.

Immobilization of catalytic species on solid supports (e.g., porous solid supports) can provide catalytic site isolation without relying on bulky ligands, thus offering an alternative route to obtaining highly active base metal catalysts. In some embodiments, for example, the presently disclosed catalysts can be prepared by metallating porous metal oxides such as, but not limited to, silica gel, mesoporous silica, zirconia, ceria, alumina, titania, or magnesia with catalyst precursors. In some embodiments, the porous metal oxides can have internal pores, cavities, and open channels to transport organic substrates and products. In some embodiments, the particle and/or pore sizes of the metal oxides can be tuned to minimize the diffusion distance needed for the organic substrates and products to maximize the catalytic turnover frequency (TOF) and total catalytic turnover number (TON).

In some embodiments, the metalation of the oxide surface can be conducted via deprotonation of surface hydroxyl groups followed by salt-metathesis with earth-abundant metal salts. In some embodiments, the presently disclosed subject matter provides uses of a metalated silica (or another metalated metal oxide) obtained by the presently disclosed methods, such as but not limited to, the catalytic organic reactions shown in Scheme 1, below, or other related reactions in a batch mode, in conventional solvents, in the absence of solvents, or in unconventional solvents, such as supercritical liquids or ionic liquids. In some embodiments, the presently disclosed subject matter provides uses of the metalated silica or other metalated metal oxide for an organic transformation, such as, but not limited to the catalytic organic reactions shown in Scheme 1 or other related reactions in a flow reactor. In some embodiments, the presently disclosed subject matter provides for the use of the metalated silica or other metalated metal oxide to catalyze sequential or multistep reactions.

The attachment of a catalytic metal onto the surface of a metal oxide isolates the catalytic sites from each other, leading to enhanced catalyst stability, which can provide for the use of earth-abundant metal catalysts for a number of reactions that are typically catalyzed by precious metal catalysts. The presently disclosed subject matter thus provides for the transition from precious metal catalysis to base metal catalysis.

III. Metalated Metal Oxide Catalysts and Methods of Preparing Same

In some embodiments, the presently disclosed subject matter provides a method of preparing a catalyst, wherein the method comprises: (a) providing a metal oxide comprising surface OH groups; and (b) reacting the metal oxide with a catalyst precursor to provide a catalyst comprising a —O-M-$L_x$ group or groups, wherein M is a catalytically active metal, each L is a metal ligand, and x is an integer between 0 and 5 (e.g., 0, 1, 2, 3, 4, or 5). Suitable metal oxides comprise materials that include oxides of metal or metalloid ions. For example, the metal oxide can be an oxide of a metal ion or of a silicon ion. In some embodiments, the term "metal oxide" can include an oxide of a metalloid ion. In some embodiments, the metal oxide is provided in particulate or powder form. In some embodiments, the particle size (e.g., the average particle size) of the metal oxide is between about 18 nm to about 5 mm (e.g., about 18 nm, 25 nm, 50 nm, 75 nm, 100 nm, 150 nm, 200 nm, 250 nm, 300 nm, 400 nm, 500 nm, 600 nm, 700 nm, 800 nm, 900 nm, 1 mm, 2 mm, 3 mm, 4 mm, or about 5 mm). For instance, nano silica can have a particle size of about 18 nm, while silica gel beads can have a particle size of about 5 mm. In some embodiments, the metal oxide is selected from the group comprising silica ($SiO_2$, e.g., silica gel, aerosol silica, mesoporous silica), zirconia ($ZrO_2$), ceria ($CeO_2$), titania ($TiO_2$), alumina ($Al_2O_3$) and magnesia (MgO). In some embodiments, the metal oxide is silica gel or mesoporous silica.

The metal oxide can be porous or non-porous. In some embodiments, the metal oxide is porous. For instance, in some embodiments, the metal oxide is mesoporous silica. In some embodiments, the mesoporous silica or other porous metal oxide can have regular hexagonal or other shaped pores with pore sizes, for example, of between 1 nanometer (nm) to tens of nms (e.g., up to about 25 nm, 50 nm, 75 nm, or about 100 nm). In some embodiments, the metal oxide has pores with pore sizes between about 2 and about 50 nm.

While the bulk of the metal oxide comprises a matrix of the metal or metalloid ion and oxygen, surfaces of the metal oxides (e.g., surfaces of a metal oxide particle as a whole and surfaces of pores within a metal oxide particle) can include hydroxyl groups attached to the metal or metalloid ion of the metal oxide matrix. These hydroxyl groups can be terminal or bridging. These hydroxyl groups can be referred to herein as "terminal hydroxyl groups" or "surface hydroxyl groups". For instance, the surface of silica particles or pores in porous silica can comprise silanol groups that are terminal (—Si—OH groups) or bridging [—Si($\mu_2$-OH)Si—].

Any suitable catalyst precursor can be used. For example, the catalyst precursor can comprise a metal complex or a hydrate or solvate thereof comprising an earth abundant and/or base metal M and metal ligands, such as, but not limited to, halides, amines, alkyl groups, aralkyl groups, aryl groups, water, hydroxyl, alkoxy, aryloxy, nitro groups, carboxylates, etc. In some embodiments, M is selected from the group comprising Mg, Zn, V, Fe, Co, Cr, Mn, Ni, and Cu. In some embodiments, M is Fe, Co or Ni.

In some embodiments, the catalyst precursor comprises a compound of the formula $ML_nX$, wherein n is an integer from 0 to 5, M is a catalytically active earth abundant/base metal (e.g., Mg, Zn, V, Fe, Co, Cr, Mn, Ni, or Cu), X is selected from the group comprising H, alkyl, aralkyl, aryl, and halo, and each L is independently selected from the group comprising H, halo, alkyl, aralkyl, aryl, heteroaryl, alkoxyl, and amine. In some embodiments, the catalyst precursor is selected from $CoCl_2$, $Me_2Mg$, $Zr(CH_2Ph)_4$, $NiCl_2$, and $FeBr_2$.

The metal oxide and the catalyst precursor can be reacted in any suitable solvent or solvent mixture (e.g., THF) at any suitable temperature. In some embodiments, more than one equivalent of the catalyst precursor (compared to the number of metal oxide OH groups) can be reacted with the metal oxide. In some embodiments, about 1.5 equivalents of the catalyst precursor (e.g., $CoCl_2$, $Me_2Mg$, $Zr(CH_2Ph)_4$, $NiCl_2$, or $FeBr_2$) can be reacted with the metal oxide. In some embodiments, the metal oxide and the catalyst precursor are reacted with one another at room temperature for between about 1 and about 12 hours (e.g., about 1, 2, 3, 4, 5, 6, 7, 8, 9, 10, 11, or 12 hours).

In some embodiments, the metal oxide is reacted with a base prior to reaction with the catalyst precursor. Reaction with the base can deprotonate one or more of the surface OH groups of the metal oxide prior to contact with the catalyst precursor to provide a deprotonated material. In some embodiments, all of the surface OH groups of the metal oxide are deprotonated by the base. In some embodiments, the base is a stronger base than hydroxide ion. For example, in some embodiments, the base can be a salt of a Group 1 element (e.g., Na, K, or Li) and a carbanion, alkoxide, amide or hydride. For example, in some embodiments, the base is sodium or potassium tert-butoxide (i.e., $NaO^tBu$ or $KO^tBu$). In some embodiments, the base is an alkyllithium, such as, but not limited to, n-butyl lithium (n-BuLi) or trimethylsilylmethyllithium ($LiCH_2SiMe_3$).

In some embodiments, at least one, two, three, four, five, ten, or more equivalents of the base (i.e., compared to the number of metal oxide surface OH groups) can be used. Reaction of the base and the metal oxide can be performed at any suitable temperature, typically at room temperature or below (e.g., between about room temperature (20-25° C.) and about −78° C.) and in any suitable organic solvent or solvent mixture (e.g., THF, THF/pentanes, THF/hexanes, benzene, etc.). In some embodiments, the metal oxide can be preheated (e.g., at about 100° C.) under vacuum for a period of time (e.g., up to about 12, 24, 36 or 48 hours) prior to reaction with the base and/or the catalyst precursor. Preheating can help to remove surface absorbed water molecules that might interfere with formation of the catalyst, activation of the catalyst, and/or use of the catalyst in a catalytic reaction.

In some embodiments, the presently disclosed subject matter provides a catalyst prepared by providing a metal oxide comprising surface hydroxyl groups and reacting the metal oxide with a catalyst precursor to form a $—OML_n$ group wherein M is a catalytically active metal, n is an integer from 0 to 5, and each L is independently selected from H, halo, alkyl, aralkyl, aryl, heteroaryl, alkoxy, and amine. In some embodiments, the presently disclosed subject matter provides a catalyst prepared by providing a metal oxide comprising surface hydroxyl groups; reacting the metal oxide with a base to deprotonate some or all of the hydroxyl groups, thereby forming a deprotonated material, and reacting the deprotonated material with a catalyst precursor.

Figure 1B:
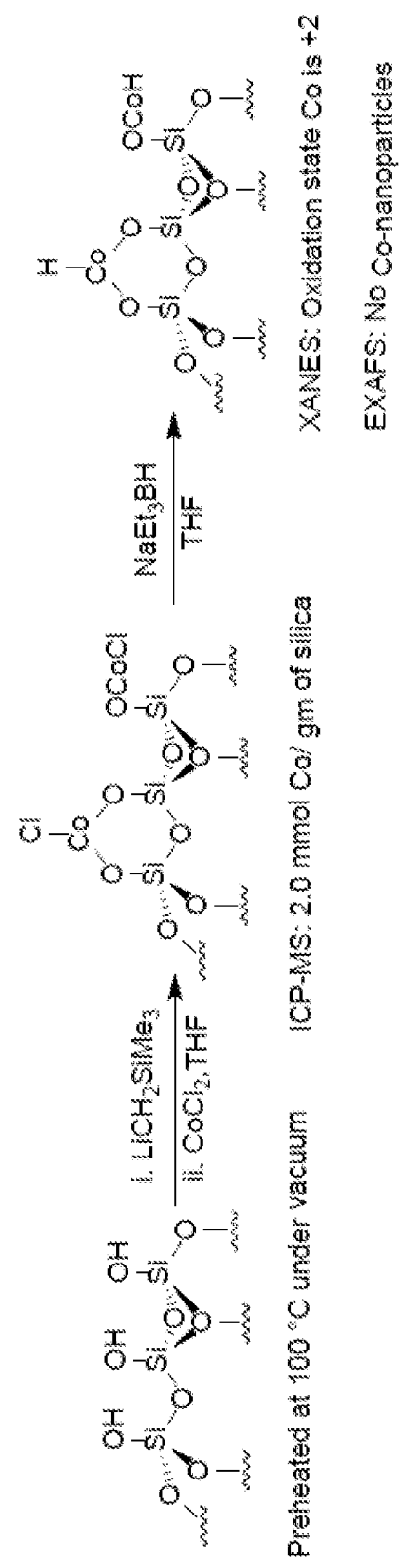
FIG. 1B is schematic drawing showing the metalation of surface silanol groups on mesoporous silica with cobalt. Silanol groups are first deprotanated using trimethylsilylmethyllithium ($LiCH_2SiMe_3$) and then reacted with cobalt chloride ($CoCl_2$). Reductive activation of the resulting cobalt halide provides a surface cobalt hydride.
Figure 1C:
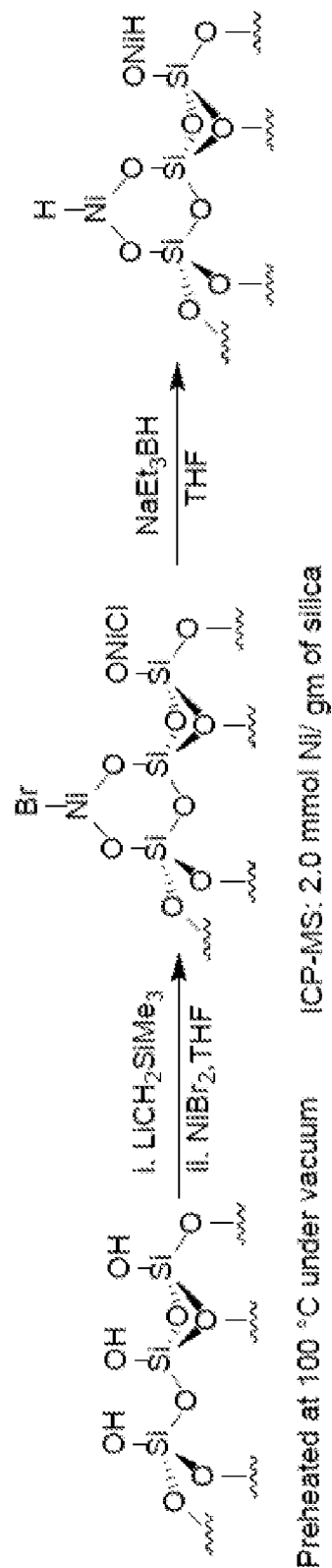
FIG. 1C is schematic drawing showing the metalation of surface silanol groups on mesoporous silica with nickel. Silanol groups are first deprotanated using trimethylsilylmethyllithium ($LiCH_2SiMe_3$) and then reacted with nickel bromide ($NiBr_2$). Reductive activation of the resulting nickel halide provides a surface nickel hydride.

FIGS. 1A-1C show schematic diagrams of the metalation of silica with Fe, Co and Ni. For instance, the structures on the left-hand side of FIGS. 1A-1C show the surfaces of a silica particle or a pore in a silica particle, wherein the surfaces comprise silanol groups. After treatment with $LiCH_2SiMe_3$ to deprotonate the silanol groups, the deprotonated silica is reacted with a metal complex comprising an earth-abundant metal (i.e., $FeBr_2$, $CoCl_2$, or $NiBr_2$) to provide a metalated silica as shown in the structures in the middle of each of FIGS. 1A-1C. The metalated silica comprises surface —OML groups, wherein M is the metal from the metal complex and L is a ligand from the metal complex. In some embodiments, the earth abundant metal ions can be bonded to either one or two surface metal oxide oxygen atoms. Prior to use as a catalyst, the earth abundant metal group can be reductively activated, e.g., using an organoboron compound, such as a hydridotrialkylboronate (e.g., $NaEt_3BH$), or other reagents that can deliver a hydride (e.g., $NaBH_4$ and NaH) to form —OMH groups on the surface of the silica.

In some embodiments, the presently disclosed subject matter provides a catalyst comprising a metalated metal oxide (i.e., a metalated material of the formula $M'_yO_z$, wherein M' is a metal or metalloid ion and y and z are integers (e.g., y can be 1 or 2 and z can be 1, 2, or 3)). In some embodiments, the catalyst comprises a metal oxide, wherein one or more metal or metalloid atoms M' of the metal oxide are bonded to a group of the formula $—O-M-L_x$, wherein x is an integer from 0 to 5 (i.e., 0, 1, 2, 3, 4, or 5), M is a catalytically active earth abundant metal, and each L is independently selected from the group consisting of H, halo, alkyl, aralkyl, aryl, heteroaryl, alkoxy, and amine. In some embodiments, the oxygen atom (O) of the $—O-M-L_x$ group is an oxygen atom derived from a deprotonated terminal OH group or a deprotonated μ-OH group of the metal oxide. In some embodiments, the metal or metalloid atom M' bonded to the $—O-M-L_x$ group is a metal or metalloid atom on the outer surface of a metal oxide particle or on the surface of a pore of a metal oxide particle. By being attached to a surface of the metal oxide, the catalytically active metal M can be free of decomposition due to disproportionation, even though, in some embodiments, the same catalytically active metal or $—O-M-L_x$ group would decompose if not attached to the metal oxide surface. Accordingly, in some embodiments, the presently disclosed subject matter provides a composition of the formula $(M'_yO_z)(O-M-L_x)_q$, wherein M', M, L, y, z, and x are as defined above, and wherein q is an integer between one and the total number of surface hydroxyl groups on the metal oxide.

In some embodiments, each L of the group $—O-M-L_x$ is independently selected from H, lower alkyl (e.g., methyl or ethyl), and halo. In some embodiments, L is selected from halo (e.g., Cl or Br) and H. In some embodiments, x is 1. In some embodiments, L is H and the group $—O-M-L_x$ is —O-M-H.

In some embodiments, M is an earth abundant metal, selected from the group including, but not limited to, Fe, Co, Cr, Ni, Cu, Mn, Zr, V, and Mg. In some embodiments, M is selected from Fe, Co, and Ni. In some embodiments, the catalyst comprises between about 0.1 mmol and about 5 mmol of the catalytically active metal ion M per gram of metal oxide (e.g., about 0.1, 0.2, 0.3, 0.4, 0.5, 0.6, 0.7, 0.8, 0.9, 1.0, 1.5, 2.0, 2.5, 3.0, 3.5, 4.0, 4.5, or about 5.0 mmol of M per gram of metal oxide). In some embodiments, the catalyst comprises about 2.0 mmol of M per gram of metal oxide.

The catalyst can include any suitable metal oxide support. In some embodiments, the metal oxide is selected from the group including, but not limited to, silica ($SiO_2$, e.g., silica gel, aerosol silica, mesoporous silica), zirconia ($ZrO_2$), ceria ($CeO_2$), titania ($TiO_2$), alumina ($Al_2O_3$) and magnesia (MgO). Thus, in some embodiments, the metal or metalloid ion of the metal oxide is selected from the group comprising Si, Zr, Ce, Ti, Al, and Mg. In some embodiments, the metal oxide is silica gel or mesoporous silica.

The metal oxide can be porous or non-porous. In some embodiments, the metal oxide is porous. For instance, in some embodiments, the metal oxide is mesoporous silica. In some embodiments, the mesoporous silica or other porous metal oxide can have regular hexagonal pores with pore sizes, for example, of between 1 nanometer (nm) to tens of nms (e.g., up to about 25 nm, 50 nm, 75 nm, or about 100 nm). In some embodiments, the metal oxide has pores with pore sizes between about 2 and about 50 nm.

IV. Catalytic Reactions

A number of high production volume (HPV) chemicals, including but not limited to adipic acid and cyclohexylamine, are the products of processes involving a hydrogenation reaction. For example, adipic acid is an important building block of nylon-6,6. One main route for the production of adipic acid involves the hydrogenation of benzene, followed by oxidation of the resulting cyclohexane to form a mixture of cyclohexanol and cyclohexanone, which is further oxidized to give adipic acid. Cyclohexylamine is another HPV chemical, used primarily as a corrosion inhibitor and as a vulcanization accelerator. Cyclohexylamine can be produced by the catalytic hydrogenation of aniline using a noble metal catalyst, such as a Ru or Pd catalyst.

During the hydrogenation of aniline, dicyclohexylamine is often produced as a by-product. Dicyclohexylamine is also a HPV chemical and, like cyclohexylamine, can be used as a corrosion inhibitor and a vulcanization accelerator. Dicyclohexylamine has also been produced from the hydrogenation of diphenylamine using a Ru-based catalyst. Aniline, itself, can be prepared by the hydrogenation of nitrobenzene.

Cyclohexane-1,2-dicarboxylic acid esters, such as cyclohexanedicarboxylic acid dimethyl or diethyl esters, can be used as plasticizers, and have recently found increased use as substitutes for phthalate plasticizers in plastics such as polyvinyl chloride (PVC). Phthalate plasticizers are currently forbidden for use in some countries in plastics used, for example, in toys, due to health concerns. Cyclohexane-1,2-dicarboxylic acid esters can be produced by the catalytic hydrogenation of benzene-1,2-dicarboxylic acid esters.

Additional HPV chemicals that can be produced by methods involving hydrogenation include cyclohexanedimethanol (CHDM), furfural alcohol, and 2-ethylhexanal. CHDM, for instance, is an important precursor to polyesters. In particular, it is a co-monomer for the production of polyethylene terephthalate (PET). CHDM has been produced by the two-step catalytic hydrogenation of dimethyl terephthalate (DMT), with the first step hydrogenation resulting in dimethyl 1,4-cyclohexanedicarboxylate (DMCD) and the second step providing CHDM. Furfuryl alcohol, a material used as a foundry sand binder, can be prepared by via catalytic hydrogenation of furfural. Furfural is also an important precursor for various other molecules containing furyl, furfuryl, furoyl, of furfurylidene radical. 2-Ethylhexanol is mainly used as the alcohol component for the manufacture of ester plasticizers. The industrial production of 2-ethylhexanal includes aldol condensation of butyraldehyde, followed by hydrogenation of olefin and aldehyde in two steps.

Prior catalysts for the hydrogenation reactions to prepare these HPV chemicals typically include noble metal catalysts (e.g., Pd, Pt, and/or Ru). They can also involve the use of high temperature and/or pressures or provide low turnover. In one aspect, the presently disclosed subject matter provides an earth abundant metal catalyst that can be used in hydrogenation reactions to prepare these HPV chemicals and other molecules. In some embodiments, the presently disclosed catalysts can be used at lower temperatures and/or pressures than previously reported catalysts used in the production of these chemicals. In some embodiments, the presently disclosed catalysts can provide higher turnover numbers or turnover frequencies than previous catalysts used in the production of these chemicals. In some embodiments, the presently disclosed catalysts can be used for catalytic hydrogenations involving a wider variety of substrates than prior catalysts and/or for catalyzing reactions other than hydrogenations.

In some embodiments the presently disclosed subject matter provides uses of the presently disclosed metalated metal oxide catalysts, such as but not limited to, as catalysts for the hydrogenation of an olefin, alkyne, imine, heterocycle, nitroarene, or carbonyl-containing compound, the borylation of an aromatic C—H bond, and/or one or more of the organic transformations shown in Scheme 1, below, or other related reactions in a batch mode, in conventional solvents, in the absence of solvents, or in unconventional solvents, such as supercritical carbon dioxide. In some embodiments the presently disclosed subject matter provides uses of the metalated metal oxide catalysts for catalyzing organic transformations shown in Scheme 1, or any of Tables 1-12 of the Examples below, or other related reactions in a flow reactor or a supercritical fluid reactor to enable green manufacturing of fine chemicals. In some embodiments the presently disclosed subject matter provides for the use of the presently disclosed metalated metal oxide catalysts to catalyze sequential or multistep reactions. In some embodiments the presently disclosed subject matter provides for the use of the presently disclosed metalated metal oxide catalysts in the same system to catalyze sequential or multistep reactions.

Scheme 1. Examples of organic reactions that can be catalyzed by metalated metal oxides.

Ethylene Oligomerization:

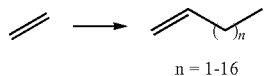

n = 1-16

Alkyne Coupling:

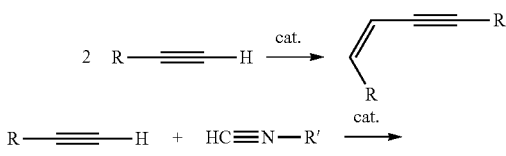

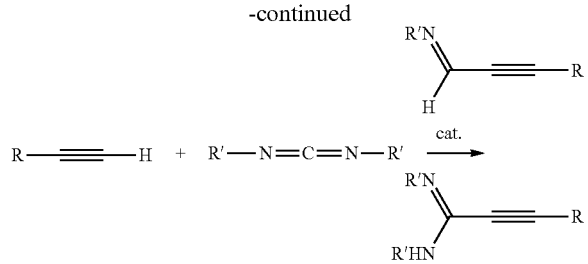

Hydromethylation:

Alkane Dehydrosilyation:

RCH₃ + HSiR'₃ ⟶ RCH₂SiR'₃ + H₂

Alkane Metathesis:

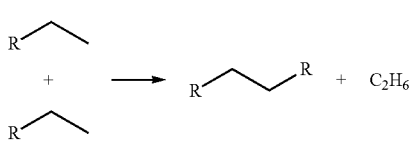

Dehydrogenative alkyl C—H phosphination:

RCH₃ + HPR'₃ ⟶ RCH₂PR'₃ + H₂

Pyridine Functionalization

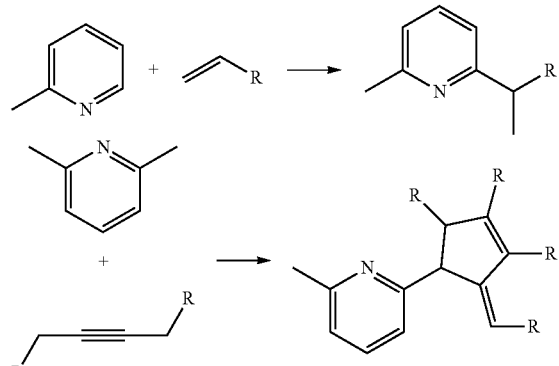

Dehydrocoupling:

R₂NH + HSiR'₃ ⟶ R₂N SiR'₃ + H₂

N₂H₄ + HSiR'₃ ⟶ H₂NHN SiR'₃ + H₂

NH₃ + HSiR'₃ ⟶ H₂N SiR'₃ + H₂

ROH + HSiR'₃ ⟶ RO SiR'₃ + H₂

B₂Pin₂ + HSiR'₃ ⟶ BPin SiR'₃ + HBpin

Hydrosilation of olefins:

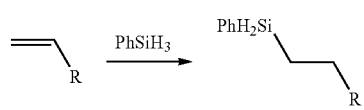

Oxidation of Primary Alcohols to Aldehydes:

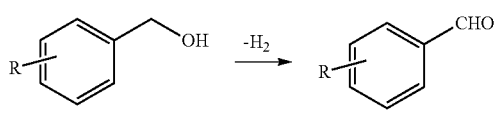

Hydroamination:

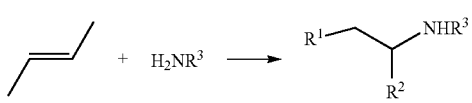

Hydroformylation:

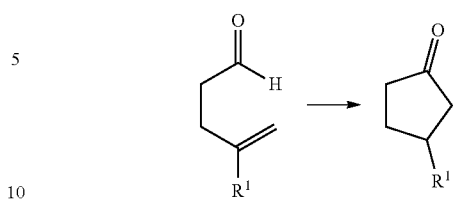

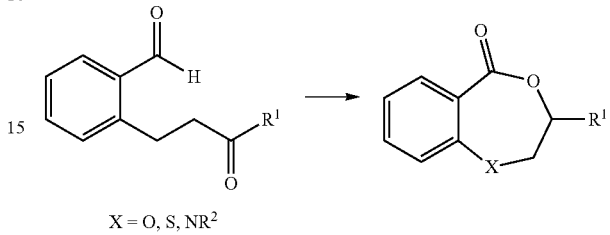

X = O, S, NR²

For instance, in some embodiments, the presently disclosed subject matter provides a method for preparing a compound comprising contacting a substrate (or substrates) capable of forming a product by catalytic transformation with a heterogeneous catalyst of the presently disclosed subject matter. In some embodiments, the catalytic transformation is selected from the group comprising alkene hydrogenation, alkyne hydrogenation, imine hydrogenation, nitrile hydrogenation, carbonyl hydrogenation, nitroarene hydrogenation, heterocycle hydrogenation, arene borylation, ethylene oligomerization, alkyne coupling, hydromethylation, alkane dehydrosilation, alkane metathesis, dehydrogenative alkyl C—H phosphination, pyridine functionalization, dehydrocoupling, hydrosilation of an olefin, ketone or aldehyde, oxidation of a primary alcohol, hydroamination, hydroformylation, C—H borylation, hydrogenation, hydroboration of a ketone or aldehyde, and C—H amination.

The contacting can take place in any suitable solvent, e.g., a solvent in which the substrate can be dissolved. In some embodiments, the solvent is an ether, such as tetrahydrofuran (THF) or dioxane; an alkane, such as a hexane (e.g., n-hexane), a heptane (e.g., n-heptane), or an octane (e.g., n-octane); a halogenated alkene, such as dichloromethane, dichloroethane, or chloroform; an aromatic solvent, such as benzene, toluene, or a xylene; DMF, dimethylsulfoxide (DMSO), an alcohol, such as methanol or ethanol; water, or mixtures thereof. In some embodiments, the solvent is an unconventional solvent, such as supercritical carbon dioxide. In some embodiments, no solvent is present (i.e., the reaction is performed "neat"). In some embodiments, the contacting takes place in the presence of a gas, such as hydrogen gas, and/or under pressure. In some embodiments, the contacting is done in conjunction with heating or cooling.

In some embodiments, the reaction is done in a flow reactor, e.g., wherein the catalyst is present in a reaction chamber into which a solvent or solvents can be pumped in and out and wherein the solvent or solvents can comprise a substrate or substrates dissolved therein. In some embodiments, the substrate and/or product is a liquid and can be pumped in and/or out of the reaction chamber in the absence of a solvent.

In some embodiments, the reaction is a hydrogenation reaction and the reaction is performed in the presence of hydrogen gas (H₂). In some embodiments, the hydrogenation reaction can be performed by activating (i.e., reductively activating) a metalated catalyst of the presently disclosed subject matter (e.g., using a borohydride such as NaEt$_3$BH) to provide a metal hydride group. The activated catalyst can be contacted with a substrate capable of undergoing a hydrogenation reaction, such as an olefin (i.e., an alkene), an alkyne, an imine, a heterocycle, a carbonyl compound (e.g., a ketone, aldehyde, ester or amide) or a nitroarene (e.g., nitrobenzene), and hydrogen gas. In some embodiments, the substrate is an olefin. In some embodiments, the substrate is a trisubstituted olefin or a tetrasubstituted olefin. The hydrogenation reaction can be performed at a pressure of between about 40 and about 200 bar (e.g., about 40, 50, 60, 70, 80, 90, 100, 110, 120, 130, 140, 150, 160, 170, 180, 190, or about 200 bar). In some embodiments, the pressure is between about 40 bar and about 120 bar. In some embodiments, the pressure is between about 40 bar and about 100 bar (e.g., about 40, 45, 50, 55, 60, 65, 70, 75, 80, 85, 90, 95, or about 100 bar). In some embodiments, the contacting can be performed for one or more hours or days, e.g., about 1 hour, 6 hours, 12 hours, 16 hours, 20 hours, 24 hours, 28 hours, 32 hours, 36 hours, 40 hours, 48 hours, 3 days, or about 4 days).

In some embodiments, the reaction can be performed at room temperature (e.g., at between about 20° C. and about 25° C.). In some embodiments, the reaction can be performed at an elevated temperature of up to about 200° C. (e.g., at about 40, 60, 80, 100, 120, 140, 160, 180 or about 200° C.).

The presently disclosed catalysts can have high turnover number (TON). For example, in some embodiments, the presently disclosed catalysts can have a TON of greater than about 50, greater than about 100, greater than about 200, greater than about 400, greater than about 1000, greater than about 10,000, greater than about 30,000, greater than about 60,000, greater than about 100,000, greater than about 200,000, greater than about 500,000, or greater than about 1,000,000.

In some embodiments, the presently disclosed catalysts can be used at low catalyst loadings, e.g., at less than about 10 mole %, less than about 5 mole %, less than about 4 mole %, less than about 3 mole %, less than about 2 mole %, less than about 1 mole %, less than about 0.5 mole %, or less than about 0.2 mole % compared to the substrate. In some embodiments, the catalysts can be used at a catalyst loading of between about 0.001 mole % and about 1.5 mole %. In some embodiments, the catalysts can be used at a catalyst loading of about 0.5 mole % or less (e.g., about 0.5, 0.4, 0.3, 0.2, 0.1, 0.09, 0.08, 0.07, 0.06, 0.05, 0.04, 0.03, 0.02, 0.01, 0.005, or about 0.001 mole % or less).

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

General Methods for Examples 2-4

All solvents were purchased from Fisher (Thermo Fisher Scientific, Waltham, Mass., United States of America) and used without further purification unless otherwise noted. All other substrates and reagents were commercially available and used as received unless otherwise indicated. $^1$H NMR spectra were recorded on a Bruker NMR 400 DRX spectrometer (Bruker Corporation, Billerica, Mass., United States of America) at 400 MHz and referenced to the proton resonance resulting from incomplete deuteration of the deuterated chloroform (δ 7.26) or deuterated DMSO (δ 2.50). Thermogravimetric analysis (TGA) was performed in air using a Shimadzu TGA-50 thermogravimetric analyzer (Shimadzu Corporation, Kyoto, Japan) equipped with a platinum pan. Powder X-ray diffraction (PXRD) patterns were collected on a Bruker D8 Venture, dual microsource (Cu and Mo) diffractometer (Bruker Corporation, Billerica, Mass., United States of America) with a CMOS detector. Cu Kα radiation was used. PXRD patterns were processed with the APEX 2 package using a PILOT plug-in. Background diffraction signals from glass capillary tubes and solvent at 2θ-20° were simulated and removed by the program PowderX. ICP-MS data were obtained with an Agilent 7700x ICP-MS (Agilent Technologies, Santa Clara, Calif., United States of America) and analyzed using ICP-MS MassHunter version B01.03. Samples were diluted in a 2% HNO$_3$ matrix and analyzed with a $^{159}$Tb internal standard against a six-point standard curve over the range from 0.1 ppb to 1000 ppb. The correlation coefficient was >0.9997 for all analytes of interest. Data collection was performed in Spectrum Mode with five replicates per sample and 100 sweeps per replicate. X-ray adsorption spectroscopy (XAS) analysis was performed at Beamline 10-BM, Advanced Photon Source (APS), Argonne National Laboratory (ANL; Lamont, Ill., United States of America).

Example 2

Synthesis of Metalated Silica

After heating at 100° C. for 24 h under vacuum, MSU-H type of mesoporous silica (80 mg, Sigma-Aldrich Company, St. Louis, Mo., United States of America) was weighed in a glove box, dispersed in dry THF, and then treated with LiCH$_2$SiMe$_3$ (1 mL, 1 mM in pentane). After reaction at room temperature for 6 h, the lithiated mesoporous silica was washed with THF five times to remove excess LiCH$_2$SiMe$_3$. The washed silica was transferred into CoCl$_2$ solution in THF (6 mL, 20 mM) and stirred for 6 h to metalate it, providing a deep blue solid. After washing with THF five times to remove excess CoCl$_2$. ICP-MS analysis of the Co-functionalized mesoporous silica gave the amount of Co content of 2.0 mmol per gm of metalated silica.

EXAFS was utilized to investigate the Co coordination environment. EXAFS spectra of CoCl@SiO$_2$ (k range 1-8 Å$^{-1}$, R range 1-5 Å) showed a strong Co—O scattering pathway at 1.4 Å (corresponding to ~1.9 Å Co—O distance) and a Co—Si second sphere scattering pathway at 2.4 Å, indicating the Co$^{2+}$ was coordinated to silicate group on the SiO$_2$ surface.

Mesoporous silica can also be functionalized with iron or nickel after treatment of lithiated silica with FeBr$_2$ or NiBr$_2$, respectively.

Example 3

Mesoporous Silica-Co Catalyzed

Hydrogenation of Olefins

General procedure of the hydrogenation of olefins using a metal-functionalized silica gel: In a nitrogen-filled glove box, silica-CoCl (0.5 mg) in 1.0 mL THF was charged into a glass vial. NaBEt$_3$H (10 μL, 1.0 M in THF) was then added to the vial and the mixture was stirred for 1 h. The solid was then centrifuged, washed twice with THF, and transferred to a glass vial in 0.5 mL THF. The olefin substrate was added to the vial. Then the vial was placed in a Parr pressure reactor, sealed under nitrogen, and charged with hydrogen to 40 bar. After stirring at room temperature for 12 h-2 d, the pressure was released and the silica catalyst was removed from the reaction mixture via centrifugation. Mesitylene (internal standard) was added to the organic extracts and the yield of the product was determined by integrating the product and mesitylene peaks in the $^1$H NMR spectra in CDCl$_3$.

A typical procedure for mesoporous-Co catalyzed hydrogenation of olefins:

Scheme 2. Hydrogenation of Trans-Methylstilbene using Co-metalated Mesoporous Silica.

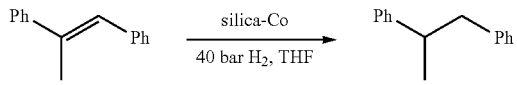

As shown in Scheme 2, above, in a glovebox, silica-CoCl in THF (0.5 mg, 0.1 mol % Co) was charged into a small vial and 0.5 mL THF was added. Then, 10 μL NaBEt$_3$H (1.0 M in THF) was added to the vial and the mixture was stirred slowly for 1 h in the glovebox. The solid was centrifuged out of suspension and washed with THF two times. Then, the black solid in 0.5 mL THF was transferred to a vial containing 0.5 mL THF solution of trans-α-methylstilbene (65.9 mg, 0.34 mmol). The vial was placed into a Parr pressure reactor in a nitrogen-filled glovebox. The reactor was then pressurized to 40 bar. After stirring at room temperature for 2 d, the solid was centrifuged out of suspension and extracted three times with THF. The combined organic extracts were concentrated in vacuo to afford crude 1,2-diphenylpropane in quantitative yield, which was sufficiently pure as analyzed by $^1$H NMR spectrum.

Summary: Upon treatment with NaEt$_3$BH, mesoporous silica-Co becomes active for catalytic hydrogenation of a range of olefins at room temperature. See Table 1, below. Tri-substituted alkenes, such as trans-α-methylstilbene, were completely hydrogenated by silica-Co in quantitative yields. See Entry 1, Table 1. Mesoporous silica-Co also completely hydrogenated tetrasubstituted alkenes, such as 2,3-dimethyl-2-butene at room temperature within 48 hours to afford 2,3-dimethylbutane. See Entry 3, Table 1. Mesoporous silica-Co is also active in hydrogenating imines, heterocycles, and nitroarenes at elevated temperatures. At a 0.5 mol % Co loading, silica-Co catalyst completely hydrogenated imine substrates, such as N-benzylidene aniline and (E)-N-(1-phenylethylidene) aniline, to afford the corresponding amines in excellent yield. See Entries 4-5, Table 1.

The hydrogenation of heterocycles can be challenging due to their resonance stabilization and due to the potential poisoning of catalysts by substrates and their products. Although significant progress has been made in developing precious metal-based molecular and heterogeneous catalysts for selective hydrogenation of N-heteroarenes, such as indoles and quinolones, the advancement of analogous earth-abundant metal catalysts has lagged behind. Catalytic hydrogenation of O-heteroarenes, such as furans and benzofurans, is also significantly underdeveloped. Additionally, hydrogenation of heteroarenes typically requires harsh reaction conditions, high catalyst loadings, and excess additives. At a 0.5 mol % Co loading, mesoporous silica-Co catalyzed hydrogenation of indole in toluene at 80° C. to afford indoline in 96% yield. See Entry 1, Table 2, below. Hydrogenation of quinolones in toluene at 80° C. gave a mixture of two products—1,2,3,4-tetrahydroquinoline and octahydroquinoline—in a 67:23 molar ratio in quantitative yield. See Entry 2, Table 2. In addition, the hydrogenation of nitrobenzene furnished aniline in moderate yields. See Entry 3, Table 2.

Figure 2:
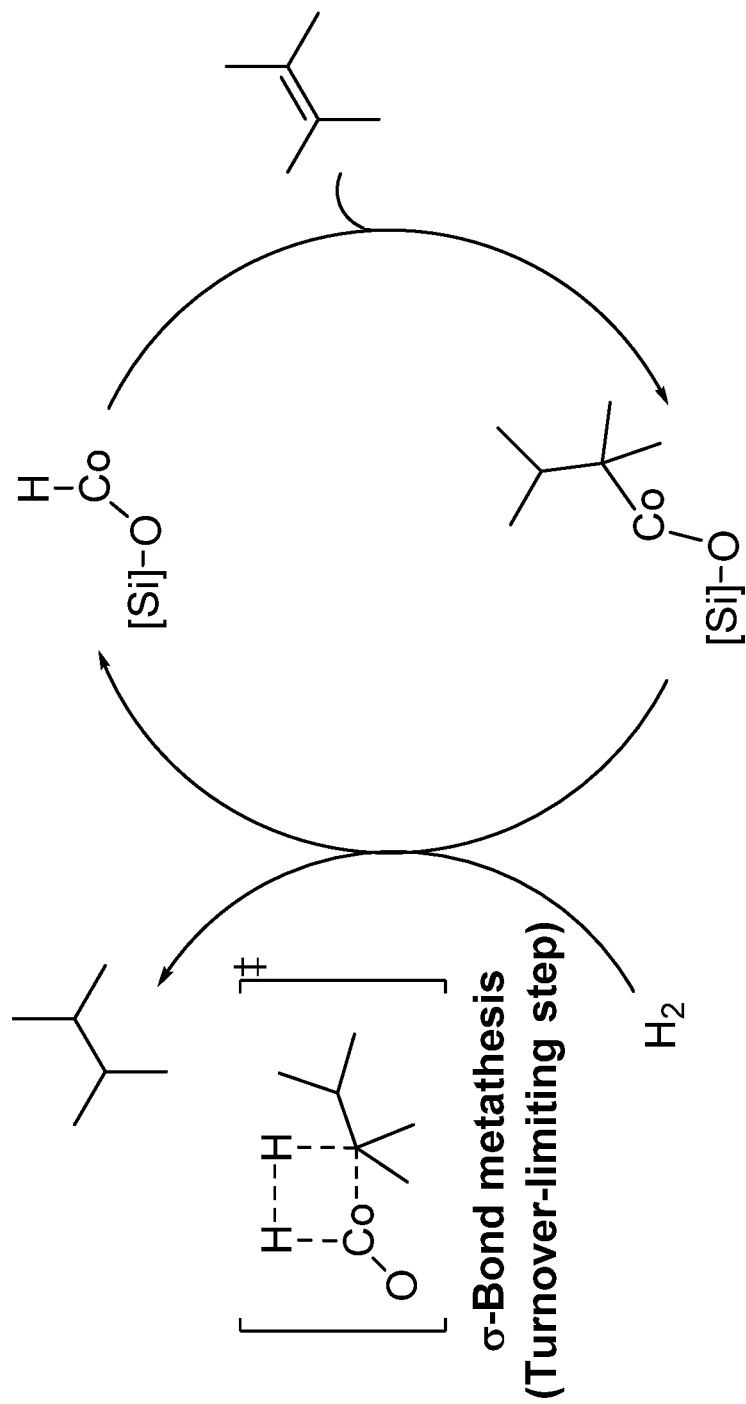
FIG. 2 is a schematic drawing showing a proposed mechanism for cobalt hydride modified silica catalyzed alkene hydrogenation via a sigma ($\sigma$)-bond methathesis pathway.

The mechanism of mesoporous silica-Co-catalyzed hydrogenation of alkenes was also studied. Treating mesoporous silica-Co with NaEt$_3$BH in THF generated silica-CoH species, which, without being bound to any one theory, is likely the active catalyst in the hydrogenation. The EXAFS spectrum of silica-Co showed the absence of Co—Co scattering from Co nanoparticles, ruling out the formation of any Co-nanoparticles within silica particles. In addition, XANES analysis of silica Co—H suggested a +2 oxidation state of Co. The activation of H$_2$ at the electron deficient Co(II)-center via oxidative addition is unlikely. The spectroscopic data thus suggests that the insertion of the C=C bond of the alkene into the Co—H bond generates a Co-alkyl intermediate, which undergoes σ-bond metathesis with H$_2$ to give an alkane product, simultaneously regenerating the cobalt-hydride species. See FIG. 2.

A Co-modified silica gel was also used for hydrogenation reactions. The cobalt functionalized silica gel was prepared by a similar method to that used for the functionalization of mesoporous silica as described in Example 1. ICP-MS analysis showed the cobalt content of 0.95 mmol per gram of metalated silica gel. Upon treatment with NaEt$_3$BH, silica gel-Co also became an active catalyst for hydrogenation of trisubstituted alkenes such as methylstilbene and indole to provide the corresponding products in good yields. See Tables 1 and 2, below.

TABLE 1

Mesoporous silica-Co and silica gel-Co catalyzed hydrogenation of olefins and imines.[a]

$$R_1R_2C=XR_3 \xrightarrow{\text{Silica-Co}}_{\text{40 bar } H_2, \text{THF}} R_1R_2CH-XR_3$$

(X = CH or N)

| Entry | Substrate | Product | % Co-loading | Time | Yield (%) |
|---|---|---|---|---|---|
| 1 | Ph-C(Me)=CH-Ph | Ph-CH(Me)-CH2-Ph | 0.05 | 40 h | 98 |
| 2[b] | Ph-C(Me)=CH-Ph | Ph-CH(Me)-CH2-Ph | 0.05 | 40 h | 100 |
| 3 | (Me)2C=C(Me)2 | (Me)2CH-CH(Me)2 | 0.05 | 40 h | 38 |
| 4 | PhCH=NPh | PhCH2-NHPh | 0.5 | 40 h | 100 |
| 5 | PhC(Me)=NPh | PhCH(Me)-NHPh | 0.5 | 40 h | 100 |

[a]Reaction conditions: 0.5 mg of mesoporous silica-CoCl, 5 equiv of NaBEt3H (1.0M in THF) w.r.t. Co, alkene, THF, 40 bar H2, 23° C.
[b]Silica gel-CoCl was used as the catalyst.

TABLE 2

Mesoporous silica-Co and silica gel-Co catalyzed hydrogenation of heterocycles and nitroarene.[a]

| Entry | Substrate | Product | % Co-loading | Time | Yield (%) |
|---|---|---|---|---|---|
| 1 | indole | indoline | 0.5 | 40 h | 96 |
| 2[b] | indole | indoline | 0.5 | 40 h | 89 |
| 2 | quinoline | 1,2,3,4-tetrahydroquinoline + decahydroquinoline | 0.5 | 40 h | 100 (67:23) |

TABLE 2-continued

Mesoporous silica-Co and silica gel-Co catalyzed hydrogenation of heterocycles and nitroarene.[a]

| Entry | Substrate | Product | % Co-loading | Time | Yield (%) |
|---|---|---|---|---|---|
| 3 | PhNO$_2$ | PhNH$_2$ | 0.5 | 40 h | 32 |

[a]Reaction conditions: 0.5 mg of mesoporous silica-CoCl, 5 equiv of NaBEt$_3$H (1.0M in THF) w.r.t. Co, alkene, THF, 40 bar H$_2$, 23° C.
[b]Silica gel-Co/cl was used as the catalyst.

Example 4

Mesoporous Silica-Co Catalyzed C—H Borylation of an Arene

A Typical procedure for mesoporous silica-Co catalyzed C—H borylation of arenes: In a glovebox, mesoporous silica-CoCl (2.0 mg) was charged into a small vial and 1.0 mL THF was added. Then, 20 μL NaBEt$_3$H (1.0 M in THF) was added to the vial and the mixture was stirred slowly for 1 h in the glovebox. The solid was centrifuged out of suspension and washed with THF twice and with arene once. B$_2$pin$_2$ in 2.0 mL arene was added to the vial and the resultant mixture was transferred to a Schlenk tube. The tube was heated to reflux under nitrogen at 100° C. for 2 d. The reaction mixture was cooled to room temperature and the solid was centrifuged out of suspension. The extract was concentrated in vacuo to give the boronate ester product.

Summary: Mesoporous silica-Co was active in the borylation of aromatic C—H bonds. See Table 3, below. At a 5 mol % Co loading, mesoporous silica-Co catalyzed the borylation reaction of benzene at 100° C. to provide phenylboronic ester in 51% yield. See Entry 1, Table 3.

TABLE 3

Mesoporous silica-Co-catalyzed borylation of aromatic C—H bonds.[a]

Ar—H (neat) + B$_2$pin$_2$ $\xrightarrow[\text{-H}_2]{\text{Mesoporous silica-Co, 100° C.}}$ Ar—Bpin

| Entry | Substrate | Product | % Co-loading | Time | Yield (%) |
|---|---|---|---|---|---|
| 1 | benzene | PhBpin | 5 | 3 d | 51 |
| 2 | biphenyl | biphenyl-Bpin | 5 | 4 d | 32 |

[a]Reaction conditions: 0.5 mg of mesoporous silica-CoCl, 5 equiv of NaBEt$_3$H (1.0M in THF) w.r.t. Co, 2 mL arene (neat), 40 bar H$_2$, 23 °C.

Example 5

General Methods for Examples 6-7

All of the reactions and manipulations were carried out under nitrogen with the use of standard inert atmosphere and Schlenk techniques. $^1$H NMR spectra were recorded on a Bruker NMR 500 DRX spectrometer (Bruker Corporation, Billerica, Mass., United States of America) at 500 MHz and referenced to the proton resonance resulting from incomplete deuteration of CDCl$_3$ (δ 7.26). The following abbreviations are used here: s: singlet, d: doublet, t: triplet, q: quartet, m: multiplet, br: broad, app: apparent. Gas chromatography (GC) data were obtained with an SHIMADZU GC-2010 Plus gas chromatograph (Shimadzu Corporation, Kyoto, Japan). ICP-MS data were obtained with an Agilent 7700x ICP-MS (Agilent Technologies, Santa Clara, Calif., United States of America) and analyzed using ICP-MS MassHunter version B01.03. Samples were diluted in a 2% $HNO_3$ matrix and analyzed with a 159Tb internal standard against a nine-point standard curve over the range from 1 ppb to 500 ppb. The correlation coefficient was >0.9997 for all analyses of interest. Data collection was performed in Spectrum Mode with five replicates per sample and 100 sweeps per replicate. X-ray absorption data were collected at Beamline 20-BM-B at the Advanced Photon Source (APS) at Argonne National Laboratory (Lamont, Ill., United States of America). Hydrogenation reactions were carried out in a Parr 5050 Vessel (Parr Instrument Company, Moline, Ill., United States of America) and using a Parr 5000 Multiple Reactor System (Parr Instrument Company, Moline, Ill., United States of America). Tetrahydrofuran (THF) was purified by passing through a neutral alumina column under $N_2$. Dimethylacetamide (DMA) was distilled over $CaH_2$. Benzene was dried over sodium. Silica gel was purchased from MACHEREY-NAGEL (MACHEREY-NAGEL, Inc., Bethlehem, Pa., United States of America) and dried under vacuum at 120° C. for 24 h before use. $NiBr_2$.DME was purchased from Strem Chemicals (Newburyport, Mass., United States of America).

Example 6

Synthesis of Nickel Metalated Silica

Synthesis of NiBr@$SiO_2$: Method 1: A mixture of silica gel (600 mg) and $LiCH_2SiMe_3$ (9.0 mL, 1.0 M in pentane) in THF (30 mL) was stirred for 12 h. The lithiated silica gel was washed with THF 5 times, and then $NiBr_2$.DME (416.7 mg) in a mixture of DMA (67 mL) and THF (67 mL) was added. After being stirred for 12 h, the resulting solid was washed with DMA, THF, and benzene 5 times and dried with ice/NaCl bath to give NiBr@$SiO_2$ (668 mg). ICP-MS analysis gave the amount of Ni in NiBr@$SiO_2$ (1.253 mmol Ni per g of $SiO_2$).

Method 2: A mixture of silica gel (600 mg) and KO$^t$Bu (9.0 mL, 1.0 M in THF) in THF (30 mL) was stirred for 12 h. The deprotonated silica gel was washed with THF 5 times, and then $NiBr_2$.DME (416.7 mg) in a mixture of DMA (67 mL) and THF (67 mL) was added. After being stirred for 12 h, the resulting solid was washed with DMA, THF, and benzene 5 times and dried with ice/NaCl bath to give NiBr@$SiO_2$ (690 mg). ICP-MS analysis gave the amount of Ni in NiBr@$SiO_2$ (1.250 mmol Ni per g of $SiO_2$).

XANES analysis of Ni $K_\alpha$ adsorption was employed to study Ni oxidation state in Ni@$SiO_2$ system. All NiBr@$SiO_2$, NiH@$SiO_2$, NiH@$SiO_2$-120° C. and NiH@$SiO_2$-200° C. samples showed pre-edge feature of $Ni^{2+}$ oxidation state (8331 eV), indicating no Ni nanoparticle was formed after $NaEt_3BH$ treatment or heating. EXAFS spectra of NiBr@$SiO_2$, NiH@$SiO_2$, NiH@$SiO_2$-120° C. and NiH@$SiO_2$-200° C. samples did not show any characteristic Ni—Ni scattering pathway (R=2.2 Å), also demonstrating that no Ni nanoparticle was involved in the Ni—$SiO_2$ catalytic system. EXAFS spectra of all the four samples displayed strong Ni—O scattering pathway (R=1.6 Å) and Ni—Si scattering pathway (R=2.5 Å), indicating $Ni^{2+}$ maintained coordination to silica surface after $NaEt_3BH$ treatment and heating.

Example 7

Hydrogenation Reactions Catalyzed by Nickel Metalated Silica

Hydrogenation of Aniline to form cyclohexylamine and dicyclohexylamine: In a nitrogen-filled glovebox, 2.0 mg NiBr@$SiO_2$ (2.5 µmol Ni) was weighed out in a 1.5 mL plastic centrifuge tube and added with 1 mL dry THF, followed by the addition of 25 µL of $NaEt_3BH$ (1M THF solution) at RT. After 30 mins, the activated Ni@$SiO_2$ was washed with THF by centrifugation 3 times and transferred into a reaction vessel with 2.28 mL of aniline (25 mmol). The vessel was sealed and transferred to a reactor system. Hydrogen (ultrahigh purity grade) was charged into the vessel and released to remove $N_2$ (7 times) before charging with 80 bar $H_2$. Then the vessel was disconnected from the hydrogen tank and heated. The conversion and selectivity were determined by GC-MS as shown in Table 4, below.

TABLE 4

Hydrogenation of Aniline using Metalated Silica Catalyst.

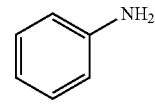

Aniline

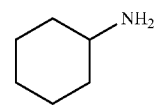

Cyclohexylamine
(CHA)

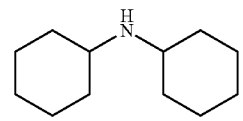

Dicyclohexylamine
(DCHA)

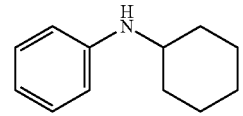

N-Phenylcyclohexylamine
(PCHA)

| Ni Loading (mol %) | T/° C. | Time | Aniline | CHA | DCHA | PCHA | TON | TOF/$h^{-1}$ |
|---|---|---|---|---|---|---|---|---|
| 0.01 | 240 | 2 h | 37.9% | 56.5% | 4.3% | 1.3% | 6370 | 3,185 |
| 0.01 | 260 | 2 h | 30.7% | 63.6% | 5.0% | 0.7% | 7100 | 3,550 |
| 0.002 | 240 | 20 h | 46.4% | 46.6% | 4.7% | 2.3% | 28,000 | 1,400 |
| 0.002 | 260 | 20 h | 27.7% | 57.2% | 13.4% | 1.7% | 37,800 | 1,890 |
| 0.005 | 240 | 40 h | 1.3% | 44.1% | 54.0% | 0.6% | 19,832 | 495.8 |

NiBr@$SiO_2$ has shown exceptionally high activity for hydrogenation of aniline. In the NiBr@$SiO_2$ system, the ratio of CHA and DCHA was tuned by using different catalyst loadings, temperatures, and reaction times.

Hydrogenation of Diethyl Phthalate: In a nitrogen-filled glovebox, 0.5 mg NiBr@SiO$_2$ (0.585 μmol Ni) was weighed out in a 1.5 mL plastic centrifuge tube and added with 1 mL dry THF, followed by the addition of 10 μL of NaEt$_3$BH (1M THF solution) at RT. After 30 mins, the activated Ni@SiO$_2$ was washed with THF by centrifugation 3 times and transferred into a reaction vessel with 4.64 mL of diethyl phthalate (23.3 mmol). The vessel was sealed and transferred to a reactor system. Hydrogen (ultrahigh purity grade) was charged into the vessel and released to remove N$_2$ (7 times) before charged with 100 bar H$_2$. Then the vessel was disconnected from the hydrogen tank and heated. The conversion and selectivity were determined by GC-MS. See Table 5, below.

TABLE 5

Hydrogenation of Diethyl Phthalate using Metalated Silica Catalyst.

| # | Ni loading/ mol % | T/ °C. | P/ bar | Time h | C/ % | D/ % | E/ % | F/ % | G/ % | H/ % |
|---|---|---|---|---|---|---|---|---|---|---|
| 1 | 0.01 | 180 | 75 | 10 | 10.79 | 0.37 | 0.22 | 0.17 | 0.74 | 87.71 |
| 2 | 0.01 | 200 | 75 | 10 | 5.89 | 2.37 | 0.70 | 0.10 | 2.30 | 88.64 |
| 3 | 0.005 | 160 | 85 | 36 | 26.9 | 0.16 | 0.04 | 0.28 | 0.44 | 72.18 |
| 4 | 0.005 | 180 | 85 | 36 | 14.31 | 1.19 | 0.37 | 0.29 | 1.62 | 82.23 |
| 5 | 0.0025 | 140 | 100 | 85 | 66.79 | 0.07 | 0.02 | 0.07 | 0.12 | 32.93 |
| 6 | 0.0025 | 160 | 100 | 85 | 42.28 | 0.16 | 0.03 | 0.14 | 0.38 | 57.01 |

Hydrogenation of 4-isopropylbenzaldehyde: In a nitrogen-filled glovebox, 1.0 mg NiBr@SiO$_2$ (1.25 μmol Ni) was weighed out in a 1.5 ml plastic centrifuge tube and added with 1 mL dry THF, followed by the addition of 25 μL of NaEt$_3$BH (1M THF solution) at RT. After 30 mins, the activated Ni@SiO$_2$ was washed with THF by centrifugation for 3 times and transferred into a reaction vessel with 1.89 mL of cuminaldehyde (12.5 mmol). The vessel was sealed and transferred to a reactor system. Hydrogen (ultrahigh purity grade) was charged into the vessel and released to remove N$_2$ (7 times) before charged with 110 bar H$_2$. Then the vessel was disconnected from the hydrogen tank and heated at 180° C. for 12 hours to give 96.7% conversion of cuminaldehyde (to form cuminyl alcohol), as determined by GC-MS. See Table 6, below.

TABLE 6

Hydrogenation of Cuminaldehyde using Metalated Silica Catalyst.

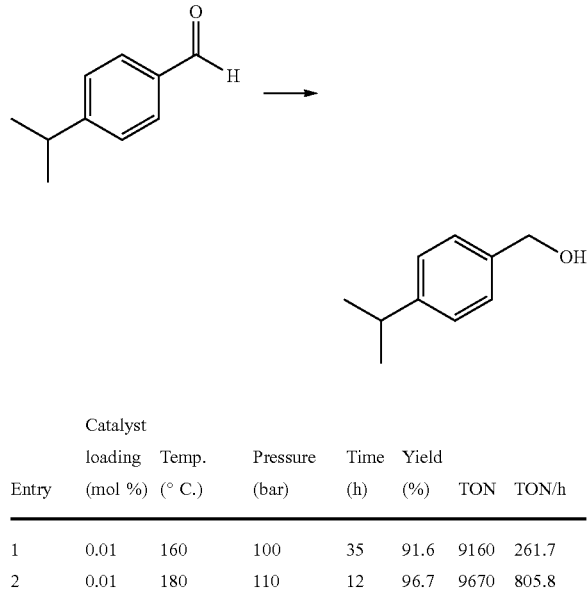

| Entry | Catalyst loading (mol %) | Temp. (° C.) | Pressure (bar) | Time (h) | Yield (%) | TON | TON/h |
|---|---|---|---|---|---|---|---|
| 1 | 0.01 | 160 | 100 | 35 | 91.6 | 9160 | 261.7 |
| 2 | 0.01 | 180 | 110 | 12 | 96.7 | 9670 | 805.8 |

Hydrogenation of mesitylene: In a nitrogen-filled glovebox, 0.5 mg NiBr@SiO$_2$ (0.585 μmol Ni) was weighed out in a 1.5 mL plastic centrifuge tube and added with 1 mL dry THF, followed by the addition of 10 μL of NaEt$_3$BH (1M THF solution) at RT. After 30 mins, the activated Ni@SiO$_2$ was washed with THF by centrifugation 3 times and transferred into a reaction vessel with 4.09 mL of mesitylene (29.25 mmol). The vessel was sealed and transferred to a reactor system. Hydrogen (ultrahigh purity grade) was charged into the vessel and released to remove N$_2$ (7 times) before charged with 55 bar H$_2$. Then the vessel was disconnected from the hydrogen tank and heated at 180° C. for 12 hours to give 100% conversion, as determined by GC-MS.

Hydrogenation of mesitylene was also run at a shorter reaction time. In a nitrogen-filled glovebox, 25 mg NiBr@SiO$_2$ (31.33 μmol Ni) was weighed out in a 1.5 mL plastic centrifuge tube and added with 1 mL dry THF, followed by the addition of 313 μL of NaEt$_3$BH (1M THF solution) at RT. After 30 mins, the activated Ni@SiO$_2$ was washed with THF by centrifugation for 3 times and transferred into a reaction vessel with 4.38 mL of mesitylene (31.3 mmol). The vessel was sealed and transferred to a reactor system. Hydrogen (ultrahigh purity grade) was charged into the vessel and released to remove N$_2$ (7 times) before charged with 100 bar H$_2$. Then the vessel was disconnected from the hydrogen tank and heated at 200° C. for 1 hour to give 100% conversion, as determined by GC-MS. See Table 7, below.

TABLE 7

Hydrogenation of Mesitylene using Metalated Silica Catalyst.

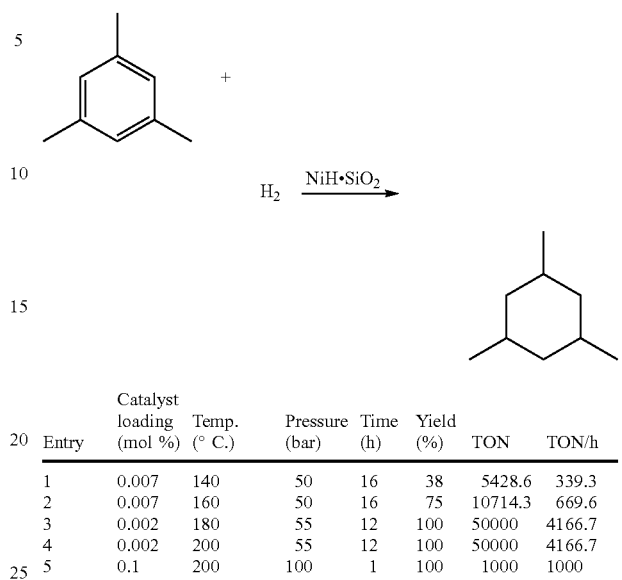

| Entry | Catalyst loading (mol %) | Temp. (° C.) | Pressure (bar) | Time (h) | Yield (%) | TON | TON/h |
|---|---|---|---|---|---|---|---|
| 1 | 0.007 | 140 | 50 | 16 | 38 | 5428.6 | 339.3 |
| 2 | 0.007 | 160 | 50 | 16 | 75 | 10714.3 | 669.6 |
| 3 | 0.002 | 180 | 55 | 12 | 100 | 50000 | 4166.7 |
| 4 | 0.002 | 200 | 55 | 12 | 100 | 50000 | 4166.7 |
| 5 | 0.1 | 200 | 100 | 1 | 100 | 1000 | 1000 |

Hydrogenation of benzene: In a nitrogen-filled glovebox, 1.0 mg NiBr@SiO$_2$ (1.17 μmol Ni) was weighed out in a 1.5 mL plastic centrifuge tube and added with 1 mL dry THF, followed by the addition of 12 μL of NaEt$_3$BH (1M THF solution) at RT. After 30 mins, the activated Ni@SiO$_2$ was washed with THF by centrifugation 3 times and transferred into a reaction vessel with 4.17 mL of benzene (46.8 mmol). The vessel was sealed and transferred to a reactor system. Hydrogen (ultrahigh purity grade) was charged into the vessel and released to remove N$_2$ (7 times) before charged with 50 bar H$_2$. Then the vessel was disconnected from the hydrogen tank and heated at 120° C. for 17 hours to give 77% yield, determined by $^1$H NMR. See Table 8, below.

TABLE 8

Hydrogenation of Benzene using Metalated Silica Catalyst.

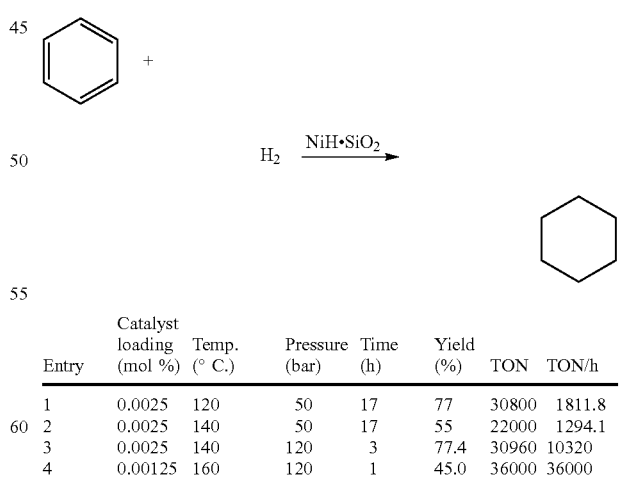

| Entry | Catalyst loading (mol %) | Temp. (° C.) | Pressure (bar) | Time (h) | Yield (%) | TON | TON/h |
|---|---|---|---|---|---|---|---|
| 1 | 0.0025 | 120 | 50 | 17 | 77 | 30800 | 1811.8 |
| 2 | 0.0025 | 140 | 50 | 17 | 55 | 22000 | 1294.1 |
| 3 | 0.0025 | 140 | 120 | 3 | 77.4 | 30960 | 10320 |
| 4 | 0.00125 | 160 | 120 | 1 | 45.0 | 36000 | 36000 |

Hydrogenation of 2-ethylhexenal: In a typical procedure for hydrogenating 2-ethylhexenal to provide 2-ethylhexanal as the major product, in a nitrogen-filled glovebox, 0.5 mg NiBr@SiO$_2$ (0.626 μmol Ni) were weighed out in a 1.5 ml plastic centrifuge tube and added with 1 mL dry THF, followed by the addition of 10 μL of NaEt$_3$BH (1M THF solution) at RT. After 30 mins, the activated Ni@SiO$_2$ was washed with THF by centrifugation for 3 times and transferred into a reaction vessel with 1.85 mL of 2-ethylhexenal (12.50 mmol). The vessel was sealed and transferred to a reactor system. Hydrogen (ultrahigh purity grade) was charged into the vessel and released to remove N$_2$ (7 times) before charged with 80 bar H$_2$. Then the vessel was disconnected from the hydrogen tank and heated at 220° C. for 12 hours to give 75.7% of 2-ethylhexanal, determined by GCMS.

In a typical procedure for hydrogenating 2-ethylhexenal to provide 2-ethylhexanol as the major product, in a nitrogen-filled glovebox, 2.0 mg NiBr@SiO$_2$ (2.506 μmol Ni) were weighed out in a 1.5 ml plastic centrifuge tube and added with 1 mL dry THF, followed by the addition of 25 μL of NaEt$_3$BH (1M THF solution) at RT. After 30 mins, the activated Ni@SiO$_2$ was washed with THF by centrifugation for 3 times and transferred into a reaction vessel with 1.85 mL of 2-ethylhexenal (12.50 mmol). The vessel was sealed and transferred to reactor system. Hydrogen (ultrahigh purity grade) was charged into the vessel and released to remove N$_2$ (7 times) before charged with 100 bar H$_2$. Then the vessel was disconnected from the hydrogen tank and heated at 220° C. for 16 hours to give 98% of 2-ethylhexanol, determined by GCMS.

Results for the hydrogenation of 2-ethylhexenal with metalated silica are summarized in Table 9, below.

TABLE 9

Hydrogenation of 2-Ethylhexenal using Metalated Silica Catalyst.

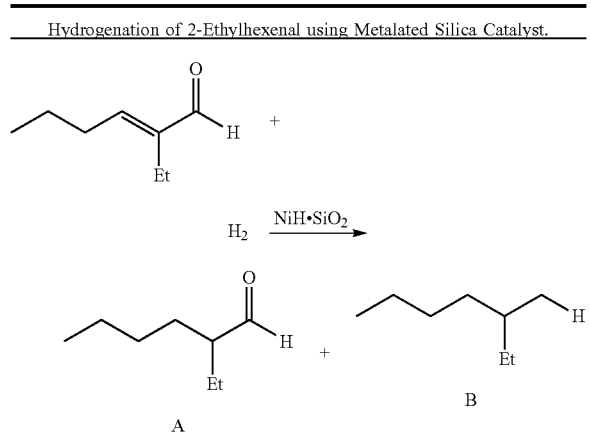

| Entry | Catalyst loading (mol %) | Temp. (° C.) | Pressure (bar) | Time (h) | Yield of A (%) | Yield of B (%) |
|---|---|---|---|---|---|---|
| 1 | 0.01 | 160 | 100 | 12 | 87 | 2 |
| 2 | 0.02 | 180 | 100 | 16 | 67.2 | 31.3 |
| 3 | 0.02 | 200 | 100 | 16 | 6.6 | 92.1 |
| 4 | 0.02 | 220 | 100 | 16 | 0.9 | 98.0 |
| 5 | 0.005 | 220 | 80 | 12 | 75.7 | 3.4 |

Hydrogenation of dimethyl terephthalate: In a nitrogen-filled glovebox, 2.5 mg NiBr@SiO$_2$ (3.133 μmol Ni) were weighed out in a 1.5 ml plastic centrifuge tube and added with 1 mL dry THF, followed by the addition of 31 μL of NaEt$_3$BH (1M THF solution) at RT. After 30 mins, the activated Ni@SiO$_2$ was washed with THF by centrifugation for 3 times and transferred into a reaction vessel with 1.22 g of dimethyl terephthalate (6.265 mmol) and EtOAc (6.2 mL). The vessel was sealed and transferred to a reactor system. Hydrogen (ultrahigh purity grade) was charged into the vessel and released to remove N$_2$ (7 times) before charged with 100 bar H$_2$. Then the vessel was disconnected from the hydrogen tank and heated at 160° C. for 42 hours to give 37% of dimethyl 1,4-cyclohexanedicarboxylate, as determined by GC-MS. See Table 10, below.

TABLE 10

Hydrogenation of Dimethyl Terephthalate using Metalated Silica Catalyst.

| Entry | Solvent | Catalyst loading (mol %) | Temp. (° C.) | Pressure (bar) | Time (h) | Yield (%) |
|---|---|---|---|---|---|---|
| 1 | EtOAc | 0.05 | 160 | 100 | 42 | 37 |
| 2 | EtOAc | 0.05 | 200 | 100 | 36 | 29 |
| 3 | 1,4-dioxane | 0.05 | 180 | 100 | 12 | 0 |
| 4 | undecane | 0.05 | 180 | 100 | 12 | 0 |

Hydrogenation of nitrobenzene: In a nitrogen-filled glovebox, 0.5 mg NiBr@SiO$_2$ (0.626 μmol Ni) were weighed out in a 1.5 ml plastic centrifuge tube and added with 1 mL dry THF, followed by the addition of 10 μL of NaEt$_3$BH (1M THF solution) at RT. After 30 mins, the activated Ni@SiO$_2$ was washed with THF by centrifugation for 3 times and transferred into a reaction vessel with 2.56 mL of nitrobenzene (25.06 mmol) and 2.28 mL of aniline (25.06 mmol). The vessel was sealed and transferred to reactor system. Hydrogen (ultrahigh purity grade) was charged into the vessel and released to remove N$_2$ (7 times) before charged with 100 bar H$_2$. Then the vessel was disconnected from the hydrogen tank and heated at 220° C. for 16 hours to give 100% of aniline, determined by GCMS. See Table 11, below.

TABLE 11

Hydrogenation of Nitrobenzene using Metalated Silica Catalyst.

| Entry | Catalyst loading (mol %) | Temp. (° C.) | Pressure (bar) | Time (h) | Yield (%) | TON | TON/h |
|---|---|---|---|---|---|---|---|
| 1 | 0.02 | 200 | 100 | 18 | 51 | 2550 | 141.7 |
| 2 | 0.05 | 180 | 100 | 12 | 12 | 240 | 20 |

TABLE 11-continued

Hydrogenation of Nitrobenzene using Metalated Silica Catalyst.

| Entry | Catalyst loading (mol %) | Temp. (° C.) | Pressure (bar) | Time (h) | Yield (%) | TON | TON/h |
|---|---|---|---|---|---|---|---|
| 3 | 0.05 | 160 | 100 | 12 | 3 | 60 | 5 |
| 4 | 0.01 | 200 | 80 | 20 | 100 | 10000 | 500 |
| 5 | 0.0025 | 220 | 80 | 16 | 100 | 40000 | 2500 |

Hydrogenation of Diisononyl Phthalate:

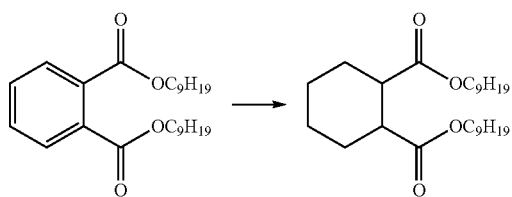

Scheme 3. Hydrogenation of Diisononyl Phthalate.

As shown in Scheme 3, above, hydrogenation of diisononyl phthalate using a metalated silica gel provided diisononyl hexahydrophthalate. More particularly, in a nitrogen-filled glovebox, 1.0 mg NiBr@SiO$_2$ (1.253 μmol Ni) were weighed out in a 1.5 ml plastic centrifuge tube and added with 1 mL dry THF, followed by the addition of 13 μL of NaEt$_3$BH (1M THF solution) at RT. After 30 mins, the activated Ni@SiO$_2$ was washed with THF by centrifugation for 3 times and transferred into a reaction vessel with 5.35 mL of diisononyl phthalate (12.53 mmol). The vessel was sealed and transferred to a reactor system. Hydrogen (ultrahigh purity grade) was charged into the vessel and released to remove N$_2$ (7 times) before charged with 100 bar H$_2$. Then the vessel was disconnected from the hydrogen tank and heated at 240° C. for 12 hours to give 80.4% of diidonoyl hexahydrophthalate, determined by $^1$H NMR.

Hydrogenation of furfural: In a nitrogen-filled glovebox, 10 mg NiBr@SiO$_2$ (12.53 μmol Ni) were weighed out in a 1.5 ml plastic centrifuge tube and added with 1 mL dry THF, followed by the addition of 125 μL of NaEt$_3$BH (1M THF solution) at RT. After 30 mins, the activated Ni@SiO$_2$ was washed with THF by centrifugation for 3 times and transferred into a reaction vessel with 2.59 mL of furfural (31.33 mmol). The vessel was sealed and transferred to a reactor system. Hydrogen (ultrahigh purity grade) was charged into the vessel and released to remove N$_2$ (7 times) before charged with 100 bar H$_2$. Then the vessel was disconnected from the hydrogen tank and heated at 160° C. for 20 hours to give 68% of furfuryl alcohol, determined by GC-MS. See Table 12, below.

TABLE 12

Hydrogenation of Furfural using Metalated Silica Catalyst.

| Entry | Catalyst loading (mol %) | Temp. (° C.) | Pressure (bar) | Time (h) | Yield (%) | TON | TON/h |
|---|---|---|---|---|---|---|---|
| 1 | 0.01 | 160 | 50 | 10 | 10 | 1000 | 100 |
| 2 | 0.04 | 160 | 100 | 20 | 68 | 1700 | 85 |
| 3 | 0.04 | 160 | 100 | 68 | 71 | 1775 | 26 |

REFERENCES

All references listed in the instant disclosure, including but not limited to all patents, patent applications and publications thereof, and scientific journal articles are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

1. U.S. Pat. No. 5,189,223A
2. US20080139383
3. U.S. Pat. No. 3,636,108
4. DE-B 1106319
5. EP-B 0053818
6. U.S. Pat. No. 5,360,934
7. U.S. Pat. No. 4,960,941
8. EP 0968996A2
9. JP68/03180
10. DE-B 1106319
11. DE-A 28 23 165
12. EP-A 07-011074
13. DE-A 12 63 296
14. U.S. Pat. No. 5,286,898
15. U.S. Pat. No. 5,319,129
16. DE-A 2823165
17. U.S. Pat. No. 3,027,398
18. U.S. Pat. No. 6,888,021B2
19. WO2014053618
20. US20120296111
21. U.S. Pat. No. 5,286,898
22. U.S. Pat. No. 4,252,689
23. U.S. Pat. No. 3,636,152
24. EP 011 090
25. U.S. Pat. No. 28,910,994
26. U.S. Pat. No. 3,270,057
27. U.S. Pat. No. 3,499,034
28. U.S. Pat. No. 4,185,036
29. DE 1277232
30. DE 2538253
31. DE 1949296

32. DE 1643856
33. DE 2832699
34. EP0968996 A2

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for preparing a catalyst, the method comprising:
    (a) providing a porous or non-porous metal oxide comprising surface OH groups, wherein said porous or non-porous metal oxide is selected from the group consisting of silica gel, aerosol silica, mesoporous silica, zirconia, ceria, titania, alumina, and magnesia;
    (b) reacting the porous or non-porous metal oxide with trimethylsilylmethyllithium ($LiCH_2SiMe_3$), thereby deprotonating all or a portion of the surface OH groups of the metal oxide to facilitate the attachment of the catalyst precursor; and
    (c) reacting the metal oxide with a catalyst precursor, wherein the catalyst precursor is a compound of the formula $ML_nX$, wherein n is an integer from 0 to 5; X is H, alkyl, aryl, or halo; M is a catalytically active metal, and each L is independently selected from the group consisting of H, halo, alkyl, aryl, heteroaryl, alkoxyl, and amine, thereby forming a catalyst comprising a —O-M-$L_x$ group, wherein x is an integer from 0 to 5.

2. The method of claim 1, wherein M is selected from the group consisting of iron, cobalt, chromium, nickel, copper, manganese, and magnesium.

3. The method of claim 1, wherein the catalyst precursor is selected from the group consisting of $CoCl_2$, $FeBr_2$, and $NiBr_2$.

* * * * *